(12) United States Patent
Ito et al.

(10) Patent No.: US 7,611,847 B2
(45) Date of Patent: Nov. 3, 2009

(54) METHOD FOR IDENTIFYING AN INTESTINAL PHENOTYPE

(75) Inventors: Yoshiaki Ito, Singapore (SG); Kosei Ito, Singapore (SG); Hiroshi Fukamachi, Tokyo (SG); Hiroshi Ida, Singapore (SG); Chohei Sakakura, Kyoto (JP); Suk-Chul Bae, Cheongju (KR)

(73) Assignee: Agency for Science, Technology and Research, Singapore (SG)

( * ) Notice: Subject to any disclaimer, the term of this patent is extended or adjusted under 35 U.S.C. 154(b) by 188 days.

(21) Appl. No.: 11/445,925

(22) Filed: Jun. 1, 2006

(65) Prior Publication Data

US 2007/0015184 A1    Jan. 18, 2007

Related U.S. Application Data

(60) Provisional application No. 60/686,243, filed on Jun. 1, 2005.

(51) Int. Cl.
  *G01N 33/53* (2006.01)
(52) U.S. Cl. .................... 435/7.1; 435/7.21; 436/501; 436/518; 422/61
(58) Field of Classification Search .................. None
  See application file for complete search history.

(56) References Cited

U.S. PATENT DOCUMENTS

| | | | | |
|---|---|---|---|---|
| 4,444,879 A | * | 4/1984 | Foster et al. | 435/7.95 |
| 7,001,882 B1 | | 2/2006 | Schlehuber | |
| 2006/0058510 A1 | | 3/2006 | Skerra et al. | |

FOREIGN PATENT DOCUMENTS

| | | |
|---|---|---|
| WO | WO 96/23879 A1 | 8/1996 |
| WO | WO 99/16873 A1 | 4/1999 |
| WO | WO 00/75308 A1 | 12/2000 |
| WO | WO 01/04144 A2 | 1/2001 |
| WO | WO 02/061069 A1 | 8/2002 |
| WO | WO 03/029462 A1 | 4/2003 |
| WO | WO 03/029463 A2 | 4/2003 |
| WO | WO 03/029471 A1 | 4/2003 |
| WO | WO 2005/019254 A1 | 3/2005 |
| WO | WO 2005/019255 A1 | 3/2005 |
| WO | WO 2005/019256 A2 | 3/2005 |
| WO | WO 2005/019256 A3 | 3/2005 |
| WO | WO 2005/115388 A1 | 12/2005 |

OTHER PUBLICATIONS

Buisine et al. (Journal of Histochemistry and Cytochemistry, Dec. 2000, vol. 48., No. 12, pp. 1657-1665).*
Silva et al. (Virchows Archiv, Mar. 2002, vol. 440, No. 3, pp. 311-317).*
Osaki et al. (European Journal of Clinical Investigation, Sep. 2004, vol. 34, No. 9, pp. 605-612).*
Babu, S.D. et al., Expression profile of mucins (MUC5AC and MUC6) in helicobacter pylori infected pre-neoplastic and neoplastic human gastric epithelium, Molecular Cancer, 5:10 doi:10.1186/1476-4598-5-10, 2006.
Bae, S.C. et al., Cloning, mapping and expression of PEBP2αC, a third gene encoding the mammalian runt domain, Gene, 159:245-248, 1995.
Baldus, S.E. et al., Correlation of MUC5AC immunoreactivity with histopathological subtypes and prognosis of gastric carcinoma, Ann. Surg. Oncol., 9(9):887-893, 2002.
Beck, F. et al., Reprogramming of intestinal differentiation and intercalary regeneration in Cdx2 mutant mice, Proc. Natl. Acad. Sci. USA, 96:7318-7323, 1999.
Beste et al., Small antibody-like proteins with prescribed ligand specificities derived from the lipocalin fold, Proc. Natl. Acad. Sci. USA, 96:1898-1903, 1999.
Birbe, M. et al., Guanylyl cyclase C is a marker of intestinal metaplasia, dysplasia, and adenocarcinoma of the gastrointestinal tract, Human Pathology, 36:170-179, 2005.
Dang, D.T. et al., Expression of the gut-enriched Krüppel-like factor (Krüppel-like factor 4) gene in the human colon cancer cell line RKO is dependent on CDX2, Oncogene 20:4884-4890, 2001.
Dudouet, B. et al., Changes in villin synthesis and subcellular distribution during intestinal differentiation of HT29-18 clones, J. Cell Biol., 105:359-369, 1987.
Fukamachi, H. et al., Mesenchymal transcription factor Fkh6 is essential for the development and differentiation of parietal cells, Biochem. Biophys. Res. Commun., 280:1069-1076, 2001.
Fukamachi, H. et al., Runx3-[1]- gastric epithelial cells differentiate into intestinal type cells, Biochem. Biophys. Res. Commun., 321:58-64, 2004.
Groisman, G.M. et al., "A valuable tool for the Light Microscopic Diagnosis of Microvillous Inclusion Disease (Familial Microvillous Atrophy)", (2002) Am. J. Surg. Pathol. 26, 902-907.
Guilford, P. et al., E-cadherin germline mutations in familial gastric cancer, Nature 392:402-405, 1998.
Herman, J.G. et al., Methylation-specific PCR: a novel PCR assay for methylation status of CpG islands, Proc. Natl. Acad. Sci. USA, 93:9821-9826, 1996.
Holt, L.J. et al., Domain antibodies: proteins for therapy, Trends Biotechnol, 21(11):484-490, 2003.

(Continued)

*Primary Examiner*—Lisa V Cook
(74) *Attorney, Agent, or Firm*—Foley & Lardner LLP

(57) ABSTRACT

The present invention relates to a method for identifying cells having a predisposition to develop an intestinal phenotype, wherein the cells are characterized by the loss of expression of the RUNX3 gene and the expression of one or more intestinal marker genes. In particular, the invention is directed to the identification of cells, which exhibit an intestinal phenotype representing a precursor of gastric cancer. Furthermore, the invention discloses a method for identifying a compound inhibiting the development of an intestinal phenotype in cells having a predisposition to develop an intestinal phenotype. Finally, the invention also relates to kits of parts for performing these methods.

13 Claims, 8 Drawing Sheets

OTHER PUBLICATIONS

Hryniewicz-Jankowska, A., et al., Ankyrins, multifunctional proteins involved in many cellular pathways., Folia Histochem. Cytobiol. 40:239-249 (*1 page only), 2002.

Ito, K. et al., Runx3, a novel tumor suppressor, is frequently inactivated in gastric cancer by protein mislocalization, Cancer Res., 65(17):7743-7750, 2005.

Ito, Y. and Miyazono, K., Runx transcription factors as key targets of TGF-β superfamily signaling, Curr. Opin, Genet. Dev. 13:43-47, 2003.

Jang, B.K. et al., Diagnostic value of endoscopic mucosal resection in low grade dysplasia of gastric mucosa, Gastrointestinal endoscopy 63(5):AB105, S1425.

Karam, S.M. and Leblond, C.P., Dynamics of epithelial cells in the corpus of the mouse stomach. I. Identification of proliferative cell types and pinpointing of the stem cell, Anat. Rec., 236:259-279, 1993.

Karlsson, N. G., et al., "Molecular characterization of the large heavily glycosylated domain glycopeptides from the rat small intestinal Much2 muchin" (1996) Glycoconjugate J. 13, 823-831.

Katz, J.P. et al., The zinc-finger transcription factor Klf4 is required for terminal differentiation of goblet cells in the colon, Development, 129:2619-2628, 2002.

Kim, H.S. et al., CDX-2 homeobox gene expression in human gastric carcinoma and precursor lesions, Journal of Gastroenterology and Hepatology, 21:438-442, 2006.

Koundrioukoff, S. et al., A direct interaction between proliferating cell nuclear antigen (PCNA) and Cdk2 targets PCNA-interacting proteins for phosphorylation, Journal of Biological Chemistry, 275(30):22882-22887, 2000.

Lauren, P., "The two histological main types of gastric carcinoma: diffuse and so-called intestinal-type carcinoma" (1965) Acta Phathol. Microbiol. Scand. 64, 31-49.

Levanon, D. et al., Runx3 knockouts and stomach cancer, Embo Rep., 4(6):560-564, 2003.

Li, Q.L. et al., Causal relationship between the loss of runx3 expression and gastric cancer, Cell, 109:113-124, 2002.

Lund, A.H. and Van Lohuizen, M., Runx: a trilogy of cancer genes, Cancer Cell, 1:213-215, 2002.

Maga, G. And Hübscher, U., J., Proliferating cell nuclear antigen 9PCNA): a dancer with many partners, Journal of Cell Science, 116(15):3051-3060, 2003.

Mashimo, H. et al., Impaired defense of intestinal mucosa in mice lacking intestinal trefoil factor, Science 274:262-265, 1996.

Mesquita P. et al., Human MUC2 mucin gene is transcriptionally regulated by Cdx homeodomain proteins in gastrointestinal carcinoma cell lines, J. Biol. Chem., 278(51):51549-51556, 2003.

Mutoh, H. et al., Conversion of gastric mucosa to intestinal metaplasia in Cdx2-expressing transgenic mice, Biochem. Biophys. Res. Commun., 294:470-479, 2002.

Nakase, Y. et al., Frequent loss of runx3 gene expression in remnant stomach cancer and adjacent mucosa with special reference to topography, British Journal of Cancer, 92:562-569, 2005.

Osaki et al., Expression of runx3 protein in human gastric mucosa, intestinal metaplasia and carcinoma, European Journal of Clinical Investigation, 34:605-612, 2004.

Peek, R.M. and Blaser, M.J., Helocobacter pylori and gastrointestinal tract adenocarcinomas, Nat. Rev. Cancer, 2:28-37, 2002.

Reis, C.A. et al., Intestinal metaplasia of human stomach displays distinct patterns of mucin (MUC1, MUC2, MUC5AC, and MUC6) expression[1], Cancer Res., 59:1003-1007, 1999.

Sakakura, C. et al., Growth inhibition and induction of differentiation of t(8;21) acute myeloid leukemia cells by the DNA-binding domain of PEBP2 and the AML1/MTG8(ETO)-specific antisense oligonucleotide, Proc. Natl. Acad. Sci. USA, 91:11723-11727, 1994.

Seno, H. et al., "CDX2 expression in the stomach with intestinal metaplasic and intestinal-type cancer: Prognostic implications" (2002) Internet Journal of Oncology, 21, 769-774.

Silberg, D.G. et al., "Cdx2 Ecotopic Expression Induces Gastric Intestinal Metaplasia in Transgenic Mice", (2002) Gastroenterology 122, 689-696.

Silverman, J. et al., Multivalent avimer proteins evolved by exon shuffing of a family of human receptor domains, Nature Biotechnology, 23(12):1556-1561, 2005.

Skerra, J., Engineered protein scaffolds for molecular recognition, Journal of Molecular Recognition 13:167-187, 2000.

Stemmermann, G.N., Intestinal metaplasia of the stomach, Cancer, 74(2):556-564, 1994.

Sugano, H. et al., "Histopathology of GI Tract Tumor", (1986) GANN Monogr. Cancer res. 31, 53-58.

Tamai, Y. et al., Clonic hamartoma development by anomalous duplication in Cdx2 knockout mice[1], Cancer Res., 59:2965-2970, 1999.

Taniuchi, I. et al., Differential requirements for Runx proteins in CD4 repression and epigenetic silencing during T lymphocyte development, Cell, 111:621-633, 2002.

Tatematsu, J. et al., Stem cells and gastric cancer: role of gastric and intestinal mixed intestinal metaplasia, Cancer Sci., 94(2):135-141, 2003.

Tierney et al., Current Medical Diagnosis & Treatment, Lange/McGraw Hill, 596-599, 2006.

Velcich, A. et al., Colorectal cancer in mice genetically deficient in the mucin Muc2, Science, 295:1726-1729, 2002.

Woolf, E. et al., Runx3 and runx1 are required for CD8 T cell development during thymopoiesis, Proc. Natl. Acad. Sci. USA, 100(13):7731-7736, 2003.

Yamachika, T. et al., Intestinal trefoil factor: a marker of poor prognosis in gastric carcinoma[1], Clin. Cancer Res., 8:1092-1099, 2002.

Yang, Q. et al., Requirement of Math1 for secretory cell lineage commitment in the mouse intestine, Science, 294:2155-2158, 2001.

Yuasa, Y., Control of gut differentiation and intestinal-type gastric carcinogenesis, Nat. Rev. Cancer, 3:592-600, 2003.

Bishop et al., Cancer Genes Come of Age, Cell, 32:1018-1020, 1983.

* cited by examiner

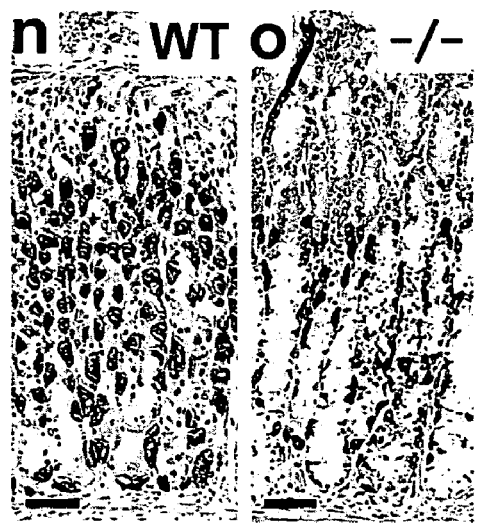
Fig. 1 (cont.)
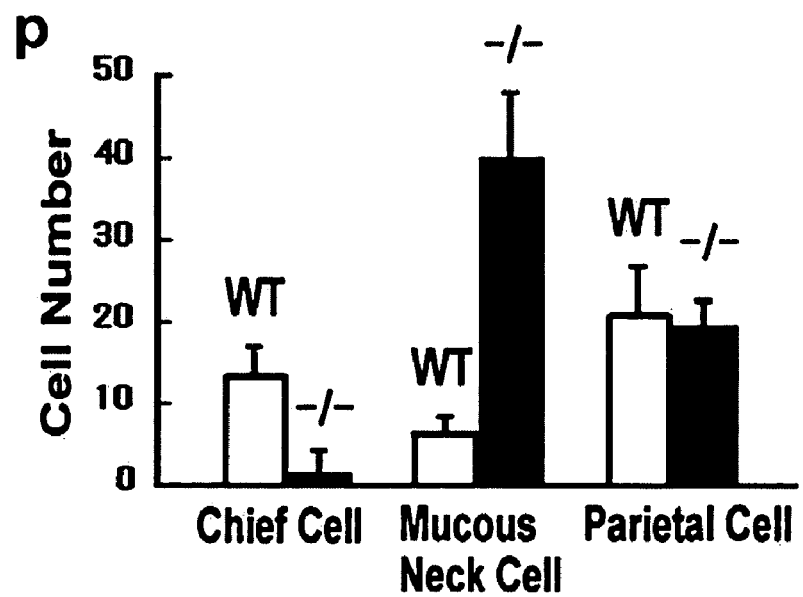

METHOD FOR IDENTIFYING AN INTESTINAL PHENOTYPE

CROSS-REFERENCE TO RELATED APPLICATIONS

This application makes reference to and claims priority of the provisional application for a "Method For Identifying An Intestinal Phenotype" filed earlier in the US Patent and Trademark Office on Jun. 1, 2005, and there duly assigned Ser. No. 60/686,243, the contents of which is incorporated herein by reference in its entirety for all purposes.

FIELD OF THE INVENTION

The present invention relates to a method for identifying cells having a predisposition to develop an intestinal phenotype, wherein the cells are characterized by the loss of expression of the RUNX3 gene and the expression of one or more intestinal marker genes. In particular, the invention is directed to the identification of cells, which exhibit an intestinal phenotype representing a precursor of gastric cancer. Furthermore, the invention provides a method for identifying a compound inhibiting the development of an intestinal phenotype in cells having a predisposition to develop an intestinal phenotype. Finally, the invention also relates to kits of parts for performing these methods.

BACKGROUND OF THE INVENTION

Gastric cancer is the second leading cause of cancer mortality worldwide, accounting for more than 650 000 deaths annually. Since gastric cancers are largely resistant to chemotherapy and radiotherapy, it is of high importance to detect the development of this neoplasm at an early stage. However, early detection of gastric cancer is uncommon.

A detection method presently used is taking x-rays (radiography) of the esophagus, the stomach, and the upper gastrointestinal tract. Administration of a barium solution, and possibly pumping air into the stomach, is carried out to assist in identifying tumors or other abnormal areas. The likelihood of detecting tumors using this method are however believed to be below 50%. A further detection method is endoscopy, an examination of the esophagus and stomach using a thin, lighted fiber optic tube termed "gastroscope". To confirm accurate diagnosis, the removal of the respective mucosal tissue by endoscopic resection is often required (for most recent data see e.g. Jang, B. K. et al. [2006] *Gastrointestinal Endoscopy* 63, 5, AB105, S1425), which coincides with cancer treatment. Other screening methods, such as radiographic fluorography or the determination of serum pepsinogen ratios of PGI to PGII, but these are rather experimental and may not detect gastric cancer in the early stages.

There are generally no symptoms in the early stages of gastric cancer, so that the cancer has in many cases spread before it is detected. When symptoms do occur, they are often so vague and nonspecific that patients ignore them. Current laboratory tests for tumor markers are of no value, unless there is already a metastatic liver spread (see e.g. Tierney et al., *Current Medical Diagnosis & Treatment* 2006, Lange/Mc Graw Hill, pages 596-599). Accordingly, detection of gastric cancer in the early stages or at the stage of intestinal metaplasia may help make routine screening easier facilitating early detection and treatment.

Colonization of the gastric mucosa by *Helicobacter pylori*, which is considered to confer a high risk for gastric cancer, is known to cause chronic gastritis followed by atrophic gastritis and intestinal metaplasia (INTESTINAL METAPLASIA). While the molecular events associated with *Helicobacter* infection have been well studied in recent years (Peek, R. M. and Blaser, M. J. (2002) *Nat. Rev. Cancer* 2, 28-37), the genetic and epigenetic changes required for the initiation of gastric carcinogenesis are still poorly understood, partly because the genes involved in the regulation of growth and differentiation of the stomach epithelium, as well as those involved in carcinogenesis, are not known.

Gastric cancer can be histologically divided into a diffuse type and an intestinal type (Lauren, P. (1965) *Acta Pathol. Microbiol. Scand.* 64, 31-49). Inactivation of the E-cadherin gene is frequently involved in the diffuse type of familial cancer (Guilford, P. et al. (1998) *Nature* 392, 402-405) as well as in sporadic cases (Yuasa, Y. (2003) *Nat. Rev. Cancer* 3, 592-600). Although genetic and epigenetic alterations in the APC, MLH1, TP53, and TGF-β type II receptor genes, and overexpression of the erbB-2 and cyclin E genes have been observed in the intestinal as well as diffuse types (Yuasa, Y. (2003), supra), they only occur in a limited number of cases and have no known roles at the initiation of carcinogenesis.

Recently, a causal relationship between the loss of expression of the Runt-related (RUNX) gene RUNX3 and gastric cancer has been identified (Li, Q. L. et al. (2002) *Cell* 109, 113-124; International Patent Application WO 02/061069, which is incorporated by reference in its entirety herein). The transcription factor subunit RUNX3, a mouse homolog of the product of the *Drosophila* segmentation gene runt, is a major nuclear target of the TGF-β signaling pathway (Lund, A. H. and van Lohuizen, M. (2002) *Cancer Cell* 1, 213-215; Ito, Y. and Miyazono, K. (2003) *Curr. Opin. Genet. Dev.* 13, 43-47). RUNX3 mediates TGF-β-induced growth inhibition and apoptosis of gastric epithelial cells. The human RUNX3 gene can be inactivated by hemizygous deletion and silencing due to hypermethylation of the promoter region in 40% of stage I and over 90% of stage IV gastric cancers, suggesting that inactivation of RUNX3 takes place in the early stages of carcinogenesis as well as during progression. The tumorigenicity in nude mice of a gastric cancer cell line that failed to express RUNX3 was strongly inhibited by the exogenous expression of RUNX3, but this inhibitory activity was not observed for a RUNX3 allele bearing a rare single amino acid substitution, R122C, which was identified in a gastric cancer patient. Furthermore, cell lines isolated from the gastric epithelium of RUNX3-/- mice were tumorigenic when injected into nude mice whereas those isolated from wild type mice were not. These results suggest that RUNX3 is a tumor suppressor of gastric cancer (Li, Q. L. et al. (2002), supra; International Patent Application WO 02/061069).

With respect to the role of RUNX3 in carcinogenesis, it has been observed that RUNX3 expression is greatly reduced in INTESTINAL METAPLASIA, a tissue frequently observed in association with gastric cancer and characterized by the morphological changes of gastric epithelial cells into cells resembling intestinal epithelial cells (Stemmermann, G. N. (1994) *Cancer* 74, 556-564). Epidemiologically, INTESTINAL METAPLASIA has been shown to be closely associated with gastric cancer (Sugano, H. et al. (1986) *GANN Monogr. Cancer Res.* 31, 53-58) and has been discussed as being indicative for the presence of a pre-cancerous state. However, opposing views persist as to the relationship between a pre-cancerous state and INTESTINAL METAPLASIA, and the nature of a relationship, if any, between INTESTINAL METAPLASIA and gastric cancer has not been established.

Accordingly, it is an object of the invention to provide a method that allows for the detection of a cell stage that corresponds to an early onset of gastric carcinogenesis.

SUMMARY OF THE INVENTION

In one aspect, the invention provides a method for identifying one or more cells having a predisposition to develop an intestinal phenotype, the method includes detecting in the one or more cells the loss of expression of the RUNX3 gene. The method also includes detecting in the one or more cells the expression of one or more intestinal marker genes.

The cells may for instance be isolated, purified and/or cultured. The cells may also be included in a mammal, such as a human.

In some embodiments, when detecting in the one or more cells the expression of one or more intestinal marker genes, also the expression of one or more gastric marker genes is detected.

In some embodiments, the method further includes comparing the result of the measurements obtained in detecting the loss of expression of the RUNX3 gene and in detecting the expression of one or more intestinal marker genes with those of obtained in a control cell.

In another aspect, the invention provides a method for identifying a compound that inhibits, or is capable of inhibiting, the development of an intestinal phenotype in one or more cells that have a predisposition to develop an intestinal phenotype. The respective cells are characterized by the loss of expression of the RUNX3 gene and by the expression of one or more intestinal marker genes. The method includes:
   (a) contacting the one or more cells with a solution supposed to contain at least one compound to be identified;
   (b) incubating the cells for a predetermined period of time; and
   (c) measuring the expression of the RUNX3 gene as well as the expression of said one or more intestinal marker genes. (b) may also include detecting the expression of one or more gastric marker genes In some embodiments the method further includes:
   (d) comparing the result of the measurement obtained in step (c) with that of a control measurement without the addition of said solution supposed to contain said at least one compound to be identified; and
   (e) identifying the compound inhibiting the development of said intestinal phenotype.

In yet another aspect, the invention provides kits of parts for performing the methods outlined above.

BRIEF DESCRIPTION OF THE DRAWINGS

The invention will be better understood with reference to the detailed description when considered in conjunction with the non-limiting examples and the drawings, in which.

DETAILED DESCRIPTION

Figure 1:
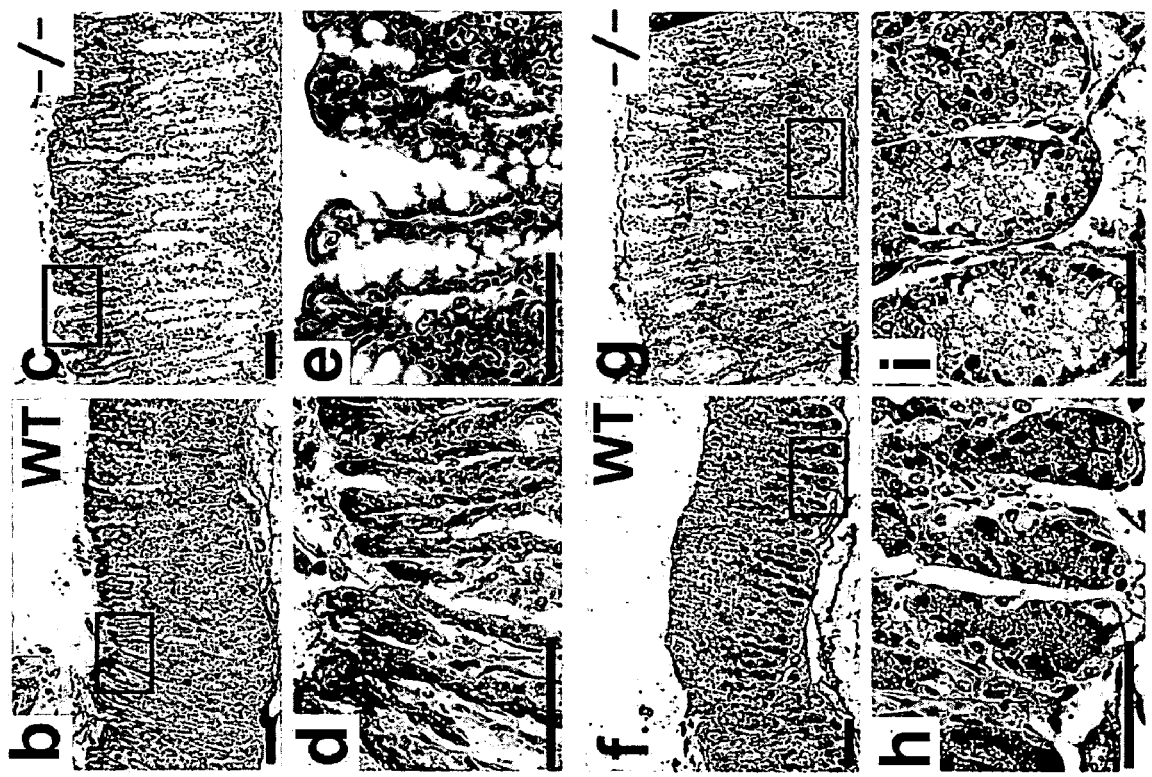
FIG. 1 depicts a diagram of a gastric gland (a) and chief cells and surface epithelial cells in the stomach of Runx3-/- mice, with immunohistochemical detection of MUC5AC (surface epithelial cells) (b-e, boxed regions in FIGS. 1b and 1c are enlarged in (d) and (e), respectively), pepsinogen (f-l, boxed regions in FIGS. 1f and 1g are enlarged in (h) and (i), (j-o) Immunohistochemical detection of chief cells (j, k), mucous neck cells (l, m) and parietal cells (n, o) with anti-pepsinogen, anti-MUC6 and anti-$H^+/K^+$ ATPase antibodies, respectively. (j-o) represent serial sections. (p) depicts the average numbers of chief cells, mucous neck cells and parietal cells in the fundic gland of 6 months-old WT and RUNX3-/- mice. (b-o) shows fundic glands of 6 months-old mice. Counter staining was done with hematoxylin (b-o). Scale bars are equal to 50 µm (d, e, h-o) and 100 µm (b, c, f, g), respectively.

The invention is based on the surprising finding that the inactivation of the RUNX3 gene expression finally results in the induction of INTESTINAL METAPLASIA in gastric epithelial cells. The term "metaplasia" is understood as a conversion from a fully differentiated cell type to another. While metaplasia may in some cases be a means of regeneration, it may likewise in other cases be an abnormal replacement of cells of one type by those of another type. Intestinal metaplasia is a conversion in morphology of gastric epithelial cells to intestinal cells. During this event gastric mucosa is replaced by epithelium that resembles the small and large bowel mucosa. Intestinal metaplasia results from gastric stem cells being diverted from a proliferation into cells that are specific for the stomach towards a proliferation into cells of the intestine, such as absorptive cells, goblet cells and Paneth cells. Since intestinal metaplasia is often associated with gastric cancer, it is usually considered as an indication of a potential risk in developing intestinal-type gastric cancer. Nevertheless, intestinal metaplasia is present in only about 20% of all gastric biopsies and it is known that only few of them progress to gastric cancer. Therefore there is a conflict of opinions among pathologists and doctors as to whether intestinal metaplasia might be considered a precancerous state or whether it is merely associated with gastric cancer without a direct link.

In view of the inventors' findings (including Osaki, M. et al. (2004), *European Journal of Clinical Investigation* 34, 605-612, incorporated herein by reference in its entirety), and considering the potential function of RUNX3 as a tumor suppressor gene, INTESTINAL METAPLASIA must be regarded as a pre-cancerous state, wherein the inactivation of RUNX 3 appears to trigger carcinogenesis. Dysplasia, which has to be considered as being one step closer to cancer, has also been found by the applicants as being characterized by a significantly reduced expression of RUNX3, when compared to normal gastric cells. In gastric cancer RUNX3 is likewise frequently inactivated (Ito, K. et al. (2005) Cancer Res. 65, 7743-7750; Nakase, Y, et al. (2005) British Journal of Cancer 92, 562-569, incorporated herein by reference in their entirety). Furthermore, the progression of INTESTINAL METAPLASIA is accompanied by the expression of several intestine-specific genes in gastric epithelial cells. These genes may thus be used as marker genes, being indicative for a predisposition of the affected cells to transform into an intestinal phenotype and provide a basis for the development of methods for identifying such cells in order to detect gastric cancer in an early stage. Therefore, the present invention allows for instance for diagnosis and subsequently carrying out methods of prevention or treatment of gastric cancer, such as for example by chemotherapy, including the activation of RUNX3 (see international patent applications WO 2005/115388 and WO 2002/061069, which are incorporated in their entirety by reference herein), at a stage where previously an individual was typically not even aware of an increased risk of, or the development of a tumor.

In a first aspect the present invention provides a method that allows for the identification of one or more cells that have a predisposition to develop an intestinal phenotype.

The term "intestinal phenotype" refers to the outward appearance of a cell or a tissue exhibiting characteristics of an intestinal cell or tissue. Beyond this morphological definition, "intestinal phenotype" also refers to the function of an intestinal cell or tissue. Examples of such phenotypes may relate to cell size (enlargement or reduction) or cell shape, cell proliferation (increase in cell number), cell differentiation (change in physiological state), cytotoxicity (cell death), apoptosis (programmed cell death) or cell survival. Typically an intestinal phenotype refers to a condition characterized by a retained capacity of the cells to proliferate, i.e. the capability of the cells to divide and to propagate. As an illustrative example, an intestinal phenotype may be a precursor of gastric cancer, which relates to any phenotype being indicative for a pre-cancerous state, i.e. an intermediate state in the transformation of a normal cell into a tumor cell. In some embodiments the intestinal phenotype is INTESTINAL METAPLASIA, a tissue frequently observed in association with gastric cancer and characterized by the morphological changes of gastric epithelial cells into cells resembling intestinal epithelial cells (Stemmermann, G. N. (1994) Cancer 74, 556-564).

The term "cell" as used herein refers to any cell or type of cell that can be subjected to the inventive methods such as an endothelial cell, an epithelial cell, a blood cell, a fibroblast, a myocyte or a neuron. In some embodiments of the invention, the one or more cells are epithelial cells, such as gastric epithelial cells, for instance secretory epithelial cells. Examples of gastric secretory epithelial cells include, but are not limited to, mucous cells, parietal cells (secreting hydrochloric acid), chief cells (secreting the proteolytic enzyme pepsin) and G cells (secreting the hormone gastrin). Mucous cells, the most abundant gastric epithelial cells, secrete a bicarbonate-rich mucus, which coats and lubricates the gastric surface, and extend down into the glands as "mucous neck cells". Thus, an illustrative example of gastric epithelial cells are gastric mucous neck cells.

The one or more cells may be derived from any mammalian species, e.g. mouse, rat, guinea pig, rabbit, goat, sheep, monkey or human. Accordingly, in some embodiments the cells are of human origin. In some embodiments the cells are in their normal physiological environment, for example included in a mammal. In some embodiments the cell(s) is/are isolated or purified. The term "purified" is understood to be a relative indication in comparison to the original environment of the cell, thereby representing an indication that the cell is relatively purer than in the natural environment. It therefore includes, but does not only refer to an absolute value in the sense of absolute purity from other cells (such as a homogeneous cell population). The term "isolated" indicates that the cell or cells has/have been removed from its/their normal physiological environment. Thus, the cell or cells may be included in a tissue sample or in an aqueous solution, or placed in a different physiological environment. In some embodiments the cell is/the cells are cultured.

The terms "expression" or "gene expression" as used herein relate to the entirety of regulatory pathways converting the information encoded in the nucleic acid sequence of a gene first into messenger RNA (mRNA) and then to a protein. Accordingly, the expression of a gene comprises its transcription into a primary hnRNA, the processing of this hnRNA into a mature RNA and the translation of the mRNA sequence into the corresponding amino acid sequence of the protein. In this context, it is also noted that the term "gene product" refers not only to a protein, including e.g. a final protein (including a splice variant thereof) encoded by that gene and a respective precursor protein where applicable, but also to the respective mRNA, which may be regarded as the "first gene product" during the course of gene expression.

The present method includes detecting the loss of expression of the RUNX3 gene in the one or more cells.

The terms "RUNX3 gene" or "RUNX3" as used herein generally refer to the human DNA- and protein sequences respectively, as described by Bae, S. C. et al. (Gene 159, 245-248 (1995)), whereof the gene has the GenBank accession number BC013362, and the protein has the UniProtKB/Swiss-Prot accession number Q13761. However, it is also understood that "RUNX 3" is not limited to the human gene and protein isoforms (e.g. GenBank accession number NM_001031680) but includes all functionally equivalent mammalian RUNX3 isoforms such as those from mouse, rat, goat or monkey, to name a few of the various isoforms. As a few illustrative examples of respective proteins shall serve the mouse protein of SwissProt accession number Q64131, the rat protein of UniProtKB/TrEMBL accession number Q91ZK1, the Mongolian jird protein of UniProtKB/TrEMBL accession number Q2 MHJ6, the Clearnose skate protein of UniProtKB/TrEMBL accession number Q6SZR4 and the Zebrafish protein of UniProtKB/TrEMBL accession number Q9DEA0.

The term "detecting" refers to any method that can be used to detect the presence of a nucleic acid (DNA and RNA) or a protein. These methods comprise established standard procedures well known in the art (cf. e.g. Ausubel, F. M. et al. (2001) Current Protocols in Molecular Biology. Wiley & Sons, Hoboken, N.J.). Examples of such methods are RT-PCR, RNAse protection assay, Northern analysis, Western analysis, ELISA, radioimmunoassay or fluorescence titration assay. The detection method may include an amplification of the signal caused by the nucleic acid or protein, such as a polymerase chain reaction (PCR) or the use of the biotinstreptavidin system, for example in form of a conjugation to an immunoglobulin. The detection method may for example include the use of an immunoglobulin, which may be linked to an attached label, such as for instance in Western analysis or ELISA. Where desired, an intracellular immunoglobulin may be used for detection. Some or all of the steps of detection may be part of an automated detection system. Illustrative examples of such systems are automated real-time PCR platforms, automated nucleic acid isolation platforms, PCR product analyzers and real-time detection systems. The detection may for instance rely on spectroscopical, photochemical, photometric, fluorometric, radiological, or enzymatic or thermodynamic means. An example of a spectroscopical detection method is fluorescence correlation spectroscopy. A photochemical method is for instance photochemical cross-linking. The use of photoactive, fluorescent, radioactive or enzymatic labels respectively are examples for photometric, fluorometric, radiological and enzymatic detection methods. An example of a thermodynamic detection method is isothermal titration calorimetry.

In one embodiment the detection is based on an antibody specific for RUNX3. Accordingly, the absence of the RUNX3 protein is determined by using such an antibody. Where a respective immunoglobulin or a fragment thereof is used, it may be generated by methods well known in the art, such as phage display (cf. also Osaki et al. (2004), *European Journal of Clinical Investigation* 34, 605-612), or may be obtained from commercial sources. Polyclonal immunoglobulins specific for RUNX3 are for example available under the product code "ab11905" from Abcam or Novus Biologicals, under the catalogue number CBFA31-A from Acris and under the catalogue number GTX11905 from GeneTex.

The term "antibody" as used herein, is understood to include an immunoglobulin and an immunoglobulin fragment that is capable of specifically binding a selected protein, e.g. RUNX3 or a protein encoded by an intestinal or a gastric marker gene, as well as a respective proteinaceous binding molecule with immunoglobulin-like functions. Examples of (recombinant) immunoglobulin fragments are Fab fragments, Fv fragments, single-chain Fv fragments (scFv), diabodies or domain antibodies (Holt, L J et al. (2003) *Trends Biotechnol.* 21(11), 484-490). An example of a proteinaceous binding molecule with immunoglobulin-like functions is a mutein based on a polypeptide of the lipocalin family. See for example Beste et al. (1999) *Proc. Natl. Acad. Sci.* USA 96, 1898-1903 and international patent applications WO 99/16873, WO 00/75308, WO 03/029471, WO 03/029462, WO 03/029463, WO 2005/019254, WO 2005/019255 or WO 2005/019256. Lipocalins described in these references such as the bilin binding protein, the human neutrophil gelatinase-associated lipocalin, human Apolipoprotein D, human tear lipocalin, or glycodelin, posses natural ligand-binding sites that can be modified so that they bind to selected small protein regions known as haptens. Other non-limiting examples of further proteinaceous binding molecules are the so-called glubodies (see WO 96/23879), proteins based on the ankyrin scaffold (Hryniewicz-Jankowska, A et al., *Folia Histochem. Cytobiol.* 40, 2002, 239-249) or crystalline scaffold (WO 01/04144,) the proteins described in Skerra, *J Mol. Recognit.* 13, 2000, 167-187, and avimers. Avimers contain so called A-domains that occur as strings of multiple domains in several cell surface receptors (Silverman, J. et al., (2005) *Nature Biotechnology,* 23, 1556-1561).

In one embodiment of the invention, the loss of expression of the RUNX3 gene is detected by measuring the degree of methylation of the exon 1 region of the RUNX3 region, wherein the term "exon" refers to a nucleic acid sequence encoding an amino acid sequence. Previously, it has been demonstrated that RUNX3 is a major growth regulator of gastric epithelial cells that is not expressed in human gastric cancer cells due to a hypermethylation of specific sequence regions termed "CpG islands" located within exon 1 of the RUNX3 gene (Li, Q. L. et al. (2002), supra). The methylation status of CpG islands can be assayed, for example, by methylation-specific PCR (Herman, J. G. et al. (1996) *Proc. Natl. Acad. Sci. USA* 93, 9821).

The present method furthermore includes detecting the expression of one or more intestinal marker genes. The terms "intestinal marker gene" and "gastric marker gene", as used herein, are understood in the context of the gastrointestinal tract. Accordingly, an intestinal marker gene is a gene that, within the gastrointestinal tract, is normally only expressed in detectable amounts—when detected by standard methods of the art—in the gut, but for instance not in the stomach. A gastric marker gene is a gene that, within the gastrointestinal tract, is normally only expressed in detectable amounts (using standard methods of the art) in the stomach, but for instance not in the gut. In some embodiments the term "intestinal marker gene" refers to any gene, which is normally specifically expressed in intestinal cells and tissues, and the expression of which is indicative of an intestinal cell phenotype. In some embodiments the term "gastric marker gene" refers to any gene, which is normally specifically expressed in gastric cells and tissues, and the expression of which is indicative of an intestinal cell phenotype. In the context of the present invention, "intestinal marker gene" particularly refers to intestine-specific genes, the expression of which is aberrantly induced in gastric cells having a predisposition to develop an intestinal phenotype. Examples of intestinal marker genes include, but are not limited to, MUC2 (e.g. Genbank accession number of a human mRNA: L21998), CDX2 (e.g. Genbank accession number of a human mRNA: NM_001265), PCNA (e.g. Genbank accession numbers of two human mRNAs: NM_002592 and NM_182649) and the guanylyl cyclase C gene (e.g. Genbank accession number of a human mRNA: U20230).

MUC2 is a member of the family of mucins—heavily glycosylated proteins that are the major components of the mucous viscous gel covering the surface of epithelial tissues (Reis, C. A. et al. (1999) *Cancer Res.* 59, 1003-1007). MUC2 is not expressed in normal gastric mucosa, but rather in intestinal goblet cells. However, in INTESTINAL METAPLASIA MUC2 expression is observed both in globet and columnar cells.

CDX2 is a gene expressed in intestinal epithelium, regulating cell proliferation and differentiation. A ParaHox gene encoding the transcription factor CDX2 is a mammalian homolog of *Drosophila* caudal, which is involved in anterior-posterior patterning. CDX2 is expressed in small and large intestines, but not in stomach and esophagus. However, CDX2 is aberrantly expressed in the human stomach in INTESTINAL METAPLASIA, dysplasia and carcinoma (Seno, H. et al. (2002) *Int. J. Oncol.* 21, 769-774; Kim, H.-S. et al. (2006) *Journal of Gastroenterology and Hepatology* 21, 438-442). The respective expression levels gradually increase from low-grade dysplasi to adenocarcinoma (Kim et al., 2006, supra). The expression of CDX2 in gastric epithelial cells of transgenic mice induces differentiation into intestinal cells (Silberg, D. G. et al. (2002) *Gastroenterology* 122, 689-696; Mutoh, H. et al. (2002) *Biochem. Biophys. Res. Commun.* 294, 470-479). Thus, CDX2 is thought to be a major inducer of the intestinal phenotype in the gut epithelium. Without the intent of being bound by theory, it is believed that there is a mechanism by which CDX2 is triggered to be expressed in stomach to induce intestinal metaplasia. The inventors' findings show that CDX2 is negatively regulated by RUNX3 and, in the absence of RUNX3, CDX2 is induced to be expressed in gastric epithelium (Fukamachi, H et al. (2004) *Biochem. Biophys. Res. Commun.* 321, 58-64, incorporated herein by reference in its entirety). As a consequence, a massive expression of intestinal markers is observed in the gastric epithelial cells of RUNX3 knockout mice. As explained below, the applicants identified two distinct levels of CDX2 expression in intestinal metaplasia. Intestinal metaplasia with the lower expression level of CDX2 is found to be particularly strongly associated with the development of gastric cancer.

The proliferating cell nuclear antigen (PCNA) was originally characterized as a DNA sliding clamp for replicative DNA polymerases and as an essential component of the eukaryotic chromosomal DNA replisome. However, subsequent studies have revealed its striking ability to interact with numerous partners, which are involved inter alia in DNA repair, chromatin remodeling, cell cycle regulation (Maga, G. and Hübscher, U. (2003) *J. Cell Sci.* 116, 3051-3060). Importantly, a direct interaction between PCNA and Cdk2 was detected which targets PCNA-interacting proteins for phosphorylation (Koundrioukoff, S. et al. (2000) *J. Biol. Chem.* 275, 22882-22887).

Guanylyl cyclase C is a member of the family of membrane bound guanylyl cyclases. serves as the receptor for the homologous diarrheagenic heat-stable enterotoxin produced by bacteria as well as for the mammalian hormones guanylin and uroguanylin. In the intestinal tract, the expression of guanylyl cyclase C, which is regulated by CDX2, is restricted to intestinal epithelial cells. Guanylyl cyclase C has meanwhile been found to be expressed on adenocarcinomas arising within intestinal metaplasia in the stomach (Birbe, M. et al. (2005) *Human Pathology* 36, 170-179).

In other embodiments of the invention, the loss of expression of the RUNX3 gene or the expression of one or more intestinal marker genes is determined by detecting the absence or presence of the respective corresponding gene products, wherein the gene product is an mRNA or a protein. For example, an mRNA can be detected by hybridization with a labeled nucleic acid probe (DNA or RNA) and subsequent analysis using either Northern blotting or performing an RNAse protection assay. Alternatively, the respective cDNA can be prepared from cellular RNA (either total RNA or mRNA) by reverse transcription and analyzed for the absence or presence of a particular nucleic acid species by PCR amplification (i.e. RT-PCR). Proteins can be conveniently detected by using specific antibodies, which may be monoclonal or polyclonal antibodies. For visualization, the antibody may be labeled or a secondary antibody conjugated to an appropriate label may be used, which binds to the specific primary antibody. Detection may be done, for example, in a Western blot-analysis or an ELISA. Suitable labels for performing the methods of the invention include enzyme labels, radioactive labels, fluorescent labels, chromogenic labels, luminescent labels, digoxigenin, biotin, small organic molecules, metals, metal complexes, and colloidal gold.

In one embodiment, the present method of the invention further includes the detection of one or more gastric marker genes. Two illustrative examples of gastric marker genes, the expression of which may be detected, are MUC6 (e.g. Genbank accession numbers of two human mRNAs: AY458429 and AY312160) and MUC5AC (e.g. Genbank accession numbers of six human mRNAs: AF043909, L46721, AJ001403, AF015521, L42292 and AJ298319).

These two proteins are also a member of the family of mucins (supra) and mainly expressed in gastric mucosa. MUC5A is particularly highly expressed in foveolar epithelium and mucous neck cells of the antrum. MUC6 is in particular expressed in the glands of the antrum. The adherent gastric mucous layer has been found to include alternating layers of MUC5AC and MUC6. Muc6 is in particular expressed in mucous neck cells and the glands of the antrum. MUC5AC is in particular expressed in the surface foveolar or pit cells of the stomach. Interestingly, the expression both mucins has not been found to be indicative of cancer previously. While the expression of MUC6 has been found not to be associated with histomorphological type or with clinicopathological features of human gastric carcinomas, even a significant reduction of MUC5AC expression has been observed in mucinous and undifferentiated carcinomas (Baldus, S. E. et al. (2002) *Ann Surg Oncol.* 9, 9, 887-893).

Generally, there can be identified one type of intestinal metaplasia, which is particularly strongly correlated with gastric cancer. The inventors have found that this type of intestinal metaplasia is characterized by relatively low levels of CDX2 expression, when compared to other types of intestinal metaplasia, and a detectable expression of both gastric mucins (e.g., MUC5AC, MUC6) and intestinal mucin (e.g. MUC2). This type, which corresponds to a type of intestinal metaplasia that is in the art described as "incomplete intestinal metaplasia", is in a precancerous state. While the complete type is characterized by the presence of absorptive cells, paneth cells and goblet cells secreting sialomucins and is similar to the small intestinal phenotype, incomplete intestinal metaplasia is characterized by the presence of columnar and goblet cells secreting sialomucins and/or sulphomucins, similar to the colonic phenotype. The two types of intestinal metaplasia can be distinguished by standard histology, histochemistry or mucin immunohistochemistry methods. The inventors furthermore found that although the incomplete intestinal metaplasia morphologically resembles colon, its CDX2 expression is significantly lower than that in normal colon.

Different types of cells in each gastric gland are believed to derive from a single progenitor cell. The uniformity of decreased CDX2 expression in every cell in the incomplete intestinal metaplasia glands (see also Tab. 1 and Tab. 2 below) indicates that the difference is caused by the different differentiation of the gastric progenitor cells. The inverse relationship between the expression of CDX2 and the expression of gastric mucins (Muc5AC and Muc6) was also found in both intestinal type and diffuse type of gastric cancer. Without intending to be bound by theory, this finding indicates that this relationship is maintained from intestinal metaplasia to gastric cancer. Thus, the decrease of CDX2 in intestinal metaplasia is a useful indicator of an increased risk of gastric cancer.

Where the expression of RUNX3 in this type of intestinal metaplasia ("incomplete") is reduced (see FIG. 8C for an example), cells become dysplastic and eventually develop into cancer cells. Accordingly, there is in particular a strong correlation between lower levels of both CDX2 and RUNX3 expression in intestinal metaplasia and a precancerous state of the gastric epithelial cells. It is noted that this type of intestinal metaplasia is always detected using the present method of the invention, regardless of whether the expression of gastric marker genes is detected or not. Where it is desired to further characterize the predisposition of cells to develop an intestinal phenotype (for example in order to estimate the likeliness of a cancerous state developing), the expression of both intestinal and gastric marker genes may be detected. As an example, the loss of expression of the RUNX3 gene as well as the expression of the intestinal marker gene MUC2, the gastric marker gene MUC5AC and the expression of the intestinal marker gene CDX2 may be detected.

Typically, an intestinal metaplasia comprises at least a part or subfraction that can be identified as the type described above ("incomplete intestinal metaplasia"). This type of intestinal metaplasia, including a respective part or subfraction, may be of any ratio to an entire intestinal metaplasia. In some embodiments, such a part or subfraction is identical with the entire intestinal metaplasia. In other embodiments a respective part or subfraction is a major part of the intestinal metaplasia, for instance between 50 and 100% thereof. In other embodiments it is only a minor part of the intestinal metaplasia, such as below 50% thereof.

The inventor's findings have in the meantime found support by data of Babu, S. D. et al (2006) *Molecular Cancer* 5, 10, doi:10.1186/1476-4598-5-10, who report decreased expression levels of MUC5AC and MUC6 in INTESTINAL METAPLASIA and dysplasia, as well as a de novo expression of MUC2.

In some embodiments of the present method the invention (as defined above), the result of the measurement obtained in detecting the loss of expression of the RUNX3 gene is compared with a corresponding result obtained in a control cell. The present applicants have shown that expression of RUNX3 is downregulated in intestinal metaplasis and gastric carcinoma (Osaki, M. (2004), supra).

In some embodiments the result of the measurement in detecting the expression of one or more intestinal marker genes is compared to a corresponding result obtained in a control cell. Likewise, the result obtained by measurements of detecting the expression of one or more gastric marker genes may be compared to results of measurements in a control cell. In some embodiments both detecting the loss of expression of the RUNX3 gene and detecting the expression of one or more intestinal marker genes are compared to the results of respective measurements of a control cell. In one embodiment all above measurements, i.e. detecting the loss of expression of the RUNX3 gene, detecting the expression of one or more intestinal marker genes, and detecting the expression of one or more gastric marker genes, are compared to corresponding results obtained using a control cell.

The term "control cell" as used herein refers to a wild-type cell having no predisposition to develop an intestinal phenotype.

In a second aspect, the invention provides a method for identifying a compound that inhibits, or is capable of inhibiting, the development of an intestinal phenotype in one or more cells that have a predisposition to develop an intestinal phenotype. The cells are characterized by the loss of expression of the RUNX3 gene and the expression of one or more intestinal marker genes as defined above. The method includes contacting the one or more cells with a solution supposed to contain at least one compound to be identified. The method further includes incubating the cells for a predetermined period of time. The method also includes measuring the expression of the RUNX3 gene as well as the expression of the respective one or more intestinal marker genes (cf. above).

In some embodiments the inventive method further includes comparing the result of the measurements obtained in detecting the loss of expression of the RUNX3 gene and the expression of one or more intestinal marker genes with corresponding results obtained in a control measurement. Such a control measurement is carried out without the addition of the solution supposed to contain the at least one compound to be identified. The method also includes identifying the compound that inhibits, or is capable of inhibiting, the development of the intestinal phenotype.

The term "compound" as used herein includes any compound inhibiting the development of an intestinal phenotype regardless whether the compound affects the expression of the RUNX3 gene and/or the expression of one or more intestinal marker genes. It is also understood that such compounds may affect any step of gene expression including transcription, RNA processing or translation or may interfere with the cellular function(s) of the respective proteins. Examples for such compounds are transcriptional enhancers or repressors, RNA-binding proteins, RNAses, factors regulating the methylation status of the RUNX3 gene sequence, anti-sense nucleic acids, small organic molecules or dominant-negative mutant proteins. Examples of compounds that may be obtained using the method of the present invention are disclosed, for example, in international patent application WO 2005/115388.

Any number of steps of the present method of the invention, including the entire method, may be performed in an automated way—also repeatedly, using for instance commercially available robots. As an illustrative example, the method may be an in-vitro screening method, for example carried out in multiple-well microplates (e.g. conventional 48-, 96-, 384- or 1536 well plates) using automated work stations. The method may also be carried out using a kit of parts, for instance designed for performing the present method.

EXEMPLARY EMBODIMENTS OF THE INVENTION

Exemplary embodiments of a method for identifying cells having a predisposition to develop an intestinal phenotype are shown in the appended figures and explained in the following.

FIG. 1 depicts chief cells and surface epithelial cells, which are prevented from differentiating in the stomach of Runx3-/- mice. (a) shows a diagram of a gastric gland. (b-e) depict the immunohistochemical detection of surface epithelial cells with an anti-MUC5AC immunoglobulin, wherein (d) and (e) represent enlargements of the boxed regions in (b) and (c), respectively. (f-i) show the immunohistochemical detection of chief cells with an anti-pepsinogen immunoglobulin, wherein (h) and (i) represent enlargements of the boxed regions in (f) and (g), respectively. (j-o) Immunohistochemical detection of chief cells (j, k), mucous neck cells (l, m) and parietal cells (n, o) with anti-pepsinogen, anti-MUC6 and anti-$H^+/K^+$ ATPase antibodies, respectively. (j-o) represent serial sections. (p) depicts the average numbers of chief cells, mucous neck cells and parietal cells in the fundic gland of 6 months-old WT and RUNX3-/- mice. (b-o) shows fundic glands of 6 months-old mice. Counter staining was done with hematoxylin (b-o). Scale bars are equal to 50 μm (d, e, h-o) and 100 μm (b, c, f, g), respectively.

Figure 2:
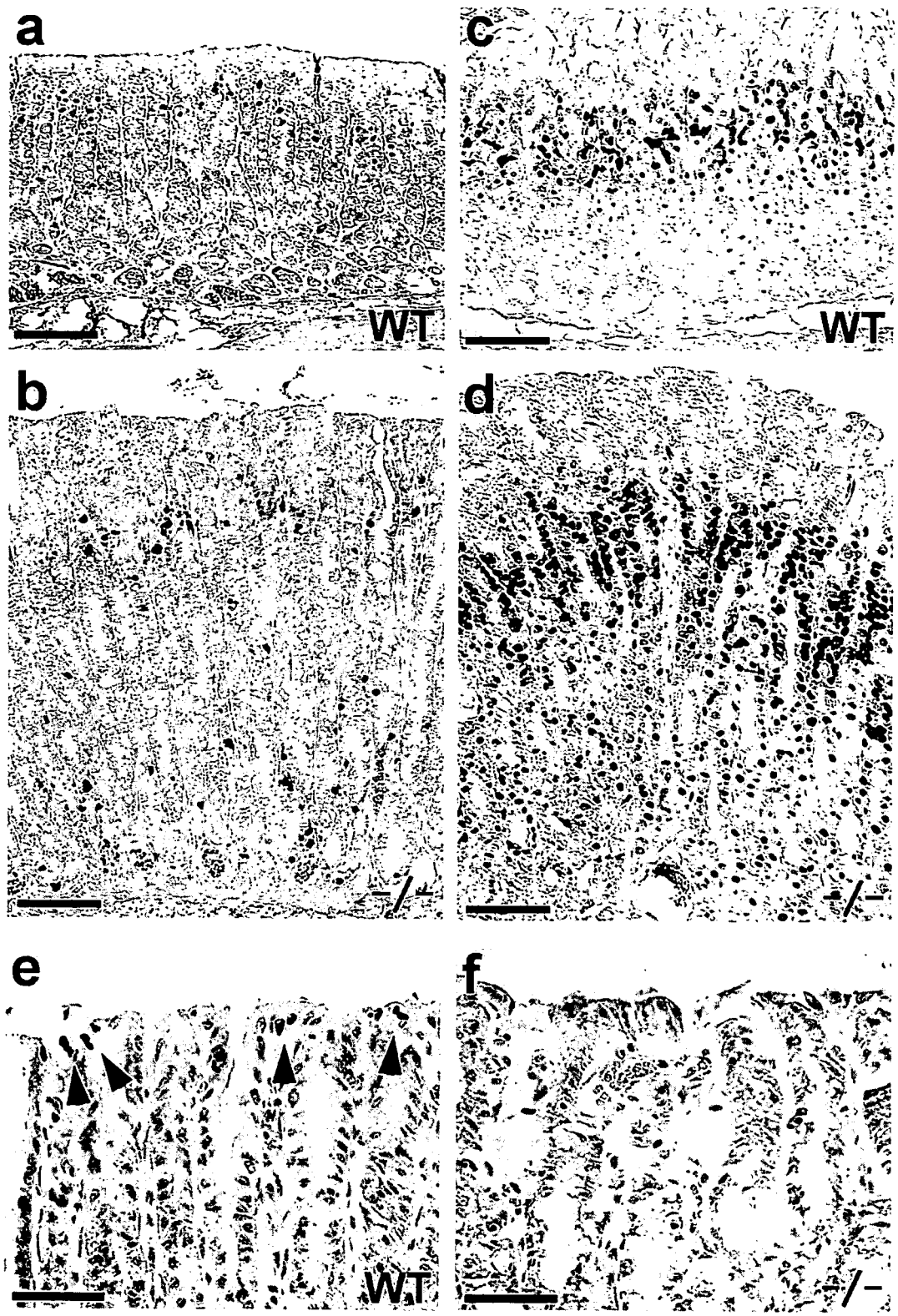
FIG. 2 depicts the cellular proliferation in the Lo and inhibition of apoptosis in the Up of Runx3-/- gastric epithelium. 5-bromo-2-deoxyuridine incorporation (a, b), PCNA immunostaining (c, d), and a DNA fragmentation detection assay (e, f) are shown.

FIG. 2 depicts the cellular proliferation in the Lo (cf. FIG. 1) and inhibition of apoptosis in the Up (cf. FIG. 1) of Runx3-/- gastric epithelium. (a, b) depict the detection of replicating cells by 5-bromo-2-deoxyuridine (BrdU) incorporation. (c, d) depict the detection of proliferating cells by immunostaining with an anti-PCNA immunoglobulin. (e, f) depict the detection of apoptotic cells using a DNA fragmentation detection assay. Arrowheads in (e) show apoptotic cells. (a-f) show fundic glands of 6 months-old mice. Counter staining was done with hematoxylin (e, f). Scale bars are equal to 50 μm (e, f) and 100 μm (a-d), respectively.

Figure 3:
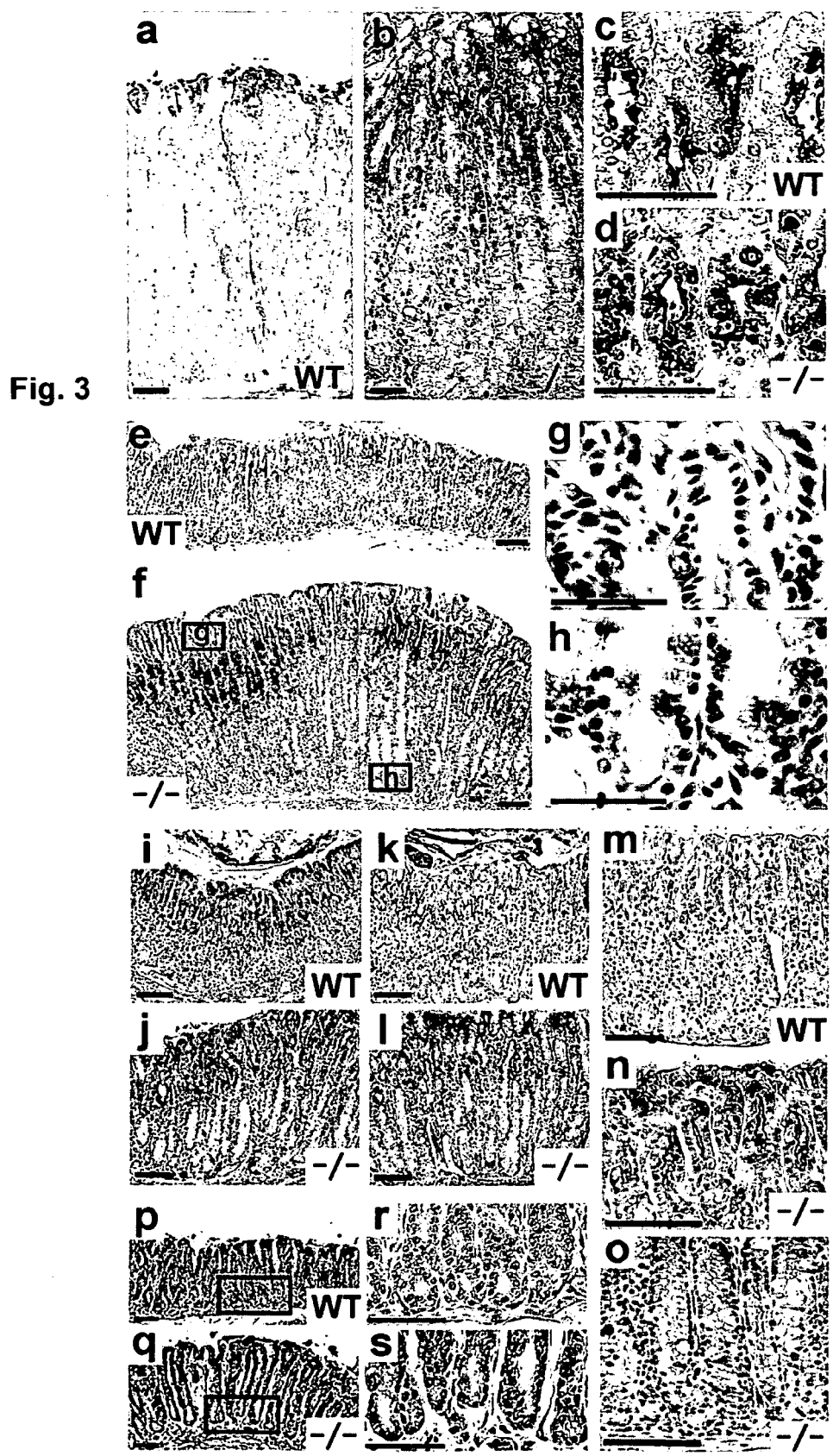
FIG. 3 shows intestinalization of RUNX3-/- gastric epithelial cells. Immunohistochemical detection of CDX2 (fundic glands of 6 months-old mice) (a, b); MUC6 immunostaining, followed by Alcian Blue staining (3 months-old gastric epithelia at the fundic area) (c, d); Alcian Blue staining (6 months-old gastric epithelia at the fundic area) (e, f, boxed regions in FIG. 3f are enlarged in g and h); and immunohistochemical detection of ITF (i, j), MUC2 (k, l), villin (m: wild-type, n: RUNX3-/- Up, o: RUNX3-/- Lo) (all fundic glands of 6 months-old mice); and immunohistochemical detection of ITF (pyloric glands of 6 months-old mice) (p, q, boxed regions in FIGS. 3p and 3q are enlarged in r and s, respectively).

FIG. 3 depicts intestinalization of RUNX3-/- gastric epithelial cells. (a, b) depict immunohistochemical detection of CDX2 in the fundic glands of 6 months-old mice. (c, d) show immunostaining with an anti-MUC6 immunoglobulin, followed by Alcian Blue staining of 3 months-old gastric epithelia at the fundic area. MUC6-positive mucous neck cells are stained brown and thus appear dark. (e, f) depicts Alcian Blue staining of 6 months-old gastric epithelia at the fundic area. (g, h) represent enlargements of the respective boxed regions in (f). (i, j) show Immunohistochemical detection of ITF in the fundic glands of 6 month-old mice. (k, l) depict immunohistochemical detection of MUC2 in fundic glands of 6 months-old mice. (m-o) show immunohistochemical detection of villin in wild-type (m) and RUNX3-/- Up (n) and Lo (o) fundic glands of 6 months-old mice. (p-s) depict Immunohistochemical detection of ITF in the pyloric glands of 6 months-old mice, wherein (r) and (s) represent enlargements of the boxed regions in (p) and (q), respectively. Counter staining was done with hematoxylin (c, d, i-s) as well as nuclear fast red (e-h). Scale bars are equal to 50 µm (a-d, g, h, p-s) and 100 µm (e, f, i-o), respectively.

Figure 4:
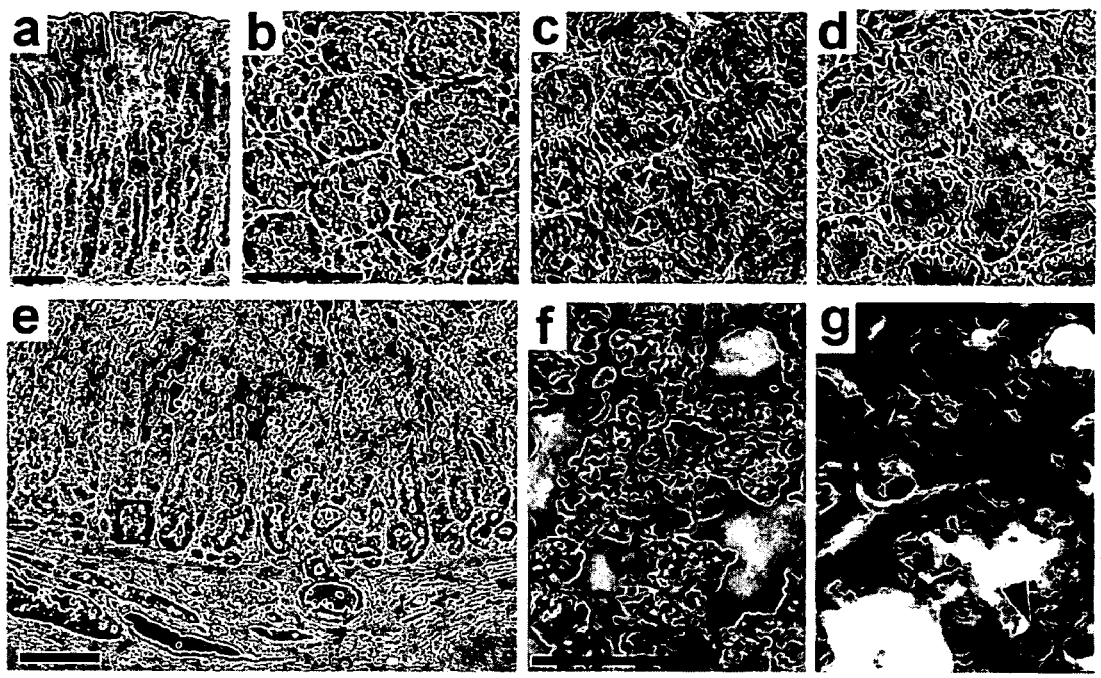
FIG. 4 shows, by immunostaining, cells with the capacity to proliferate from dysplasia in RUNX3-/- gastric epithelium, wherein an anti-MUC6 immunoglobulin, followed by Alcian Blue staining (a, e, f,), immunodetection of MUC6-expressing cells (b), double staining using Alcian Blue and an anti-CDX2 immunoglobulin (c), an anti-PCNA immunoglobulin (d), and hematoxylin and eosin staining performed on a serial section from FIG. 4f (g) were used.

FIG. 4 depicts Alcian Blue- and MUC6-positive cells with the capacity to proliferate from dysplasia in RUNX3-/- gastric epithelium. (a, e, f,) Immunostaining with an anti-MUC6 immunoglobulin, followed by Alcian Blue staining. (b) Immunodetection of MUC6-expressing cells. (c) shows double staining with Alcian Blue and an anti-CDX2 immunoglobulin. (d) depicts the detection of proliferating cells by immunostaining with an anti-PCNA immunoglobulin. (b-d) represent serial sections, which are perpendicular to the glands in the Lo. (f) represents an enlargement of the boxed region in (e). (g) shows hematoxylin and eosin staining performed on a serial section from (f). (c) shows strong (arrowheads) and weak (arrows) expression of CDX2 in Alcian Blue-positive cells. (g) shows dividing or divided cells indicated by arrowheads. (a-d) are from the fundic glands of 6 months-old mice and (e-g) from dysplasia observed in the fundic glands of 10 months-old mice. Counter staining was done with hematoxylin in (b). Scale bars are equal to 50 µm (b, f) and 100 µm (a, e), respectively.

Figure 5:
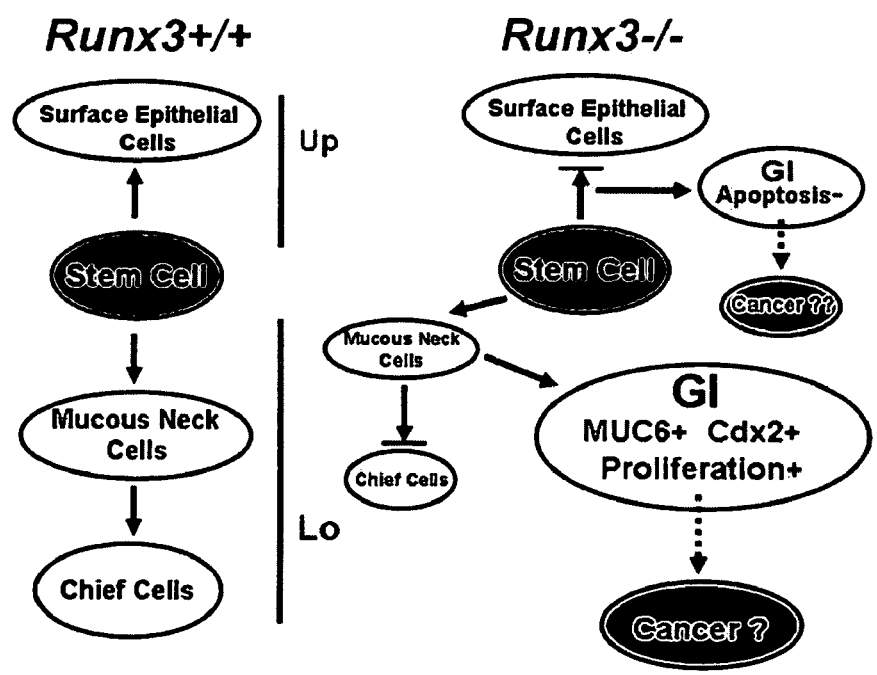
FIG. 5 depicts a model of the role of Runx3 in gastric carcinogenesis.

FIG. 5 illustrates a model of the role of Runx3 in gastric carcinogenesis. Thereby, mucous neck cells are blocked from differentiating into chief cells. At the same time, the lineage of differentiation is deregulated and these cells are induced to express intestinal (I) markers, although they continue to express a gastric (G) marker. That is, the mucous neck cells accumulating in the fundic glands in the absence of RUNX3 are no longer genuine gastric or intestinal cells. The appearance of both the gastric (G) and intestinal (I) phenotypes in a single cell or in cells of a single gastric gland is often observed for INTESTINAL METAPLASIA of the human stomach. Together with their high capacity for proliferation, the developmentally blocked abnormal mucous neck cells expressing both G and I markers observed in the RUNX3-/- stomach are likely to be pre-cancerous. Thus, RUNX3 is not only a major regulator of gastric epithelial cell growth but also a regulator of gastric epithelial cell differentiation.

Figure 6:
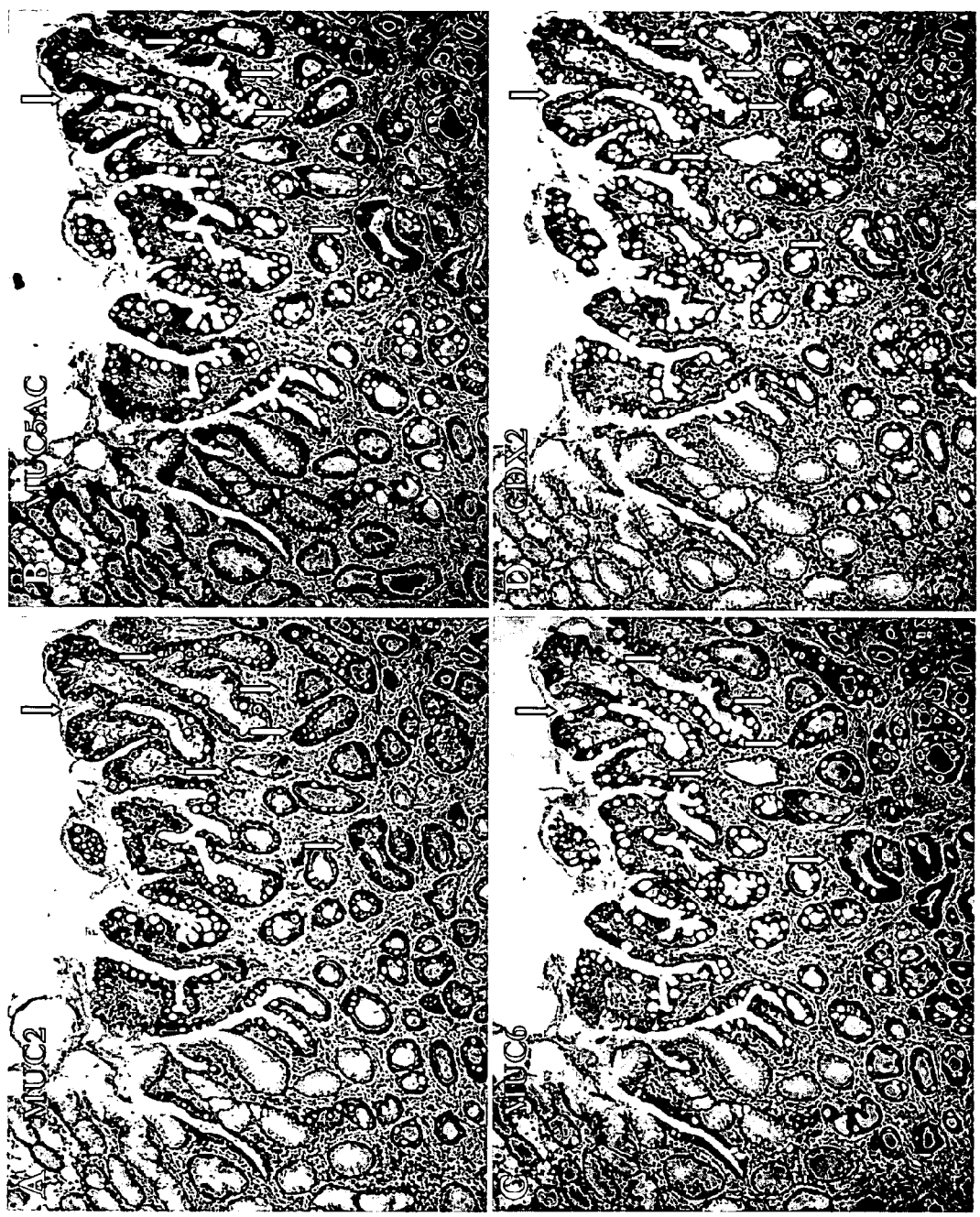
FIG. 6 depicts immunohistochemistry staining of MUC2 (A), MUC5AC (B), MUC6 (C) and CDX2 (D) in intestinal metaplasia.

FIG. 6 depicts intestinal metaplasia. MUC2 is intestinal mucin, normally not present in gastric epithelium. (A) shows the expression of MUC2 in the area which represents the entire IM in this specimen. (B) depicts MUC5AC expression. Only a subfraction of intestinal metaplasia, marked by an arrow, expresses gastric mucin. (C) shows the expression of MUC6, which is primarily expressed in the deeper gland. (D) shows the expression of CDX2. As can be seen, there are two distinct levels of CDX2 expression. Those glands that express a lower level of CDX2 also express MUC5AC (gastric mucin) as well as MUC2 (intestinal mucin).

Figure 7:
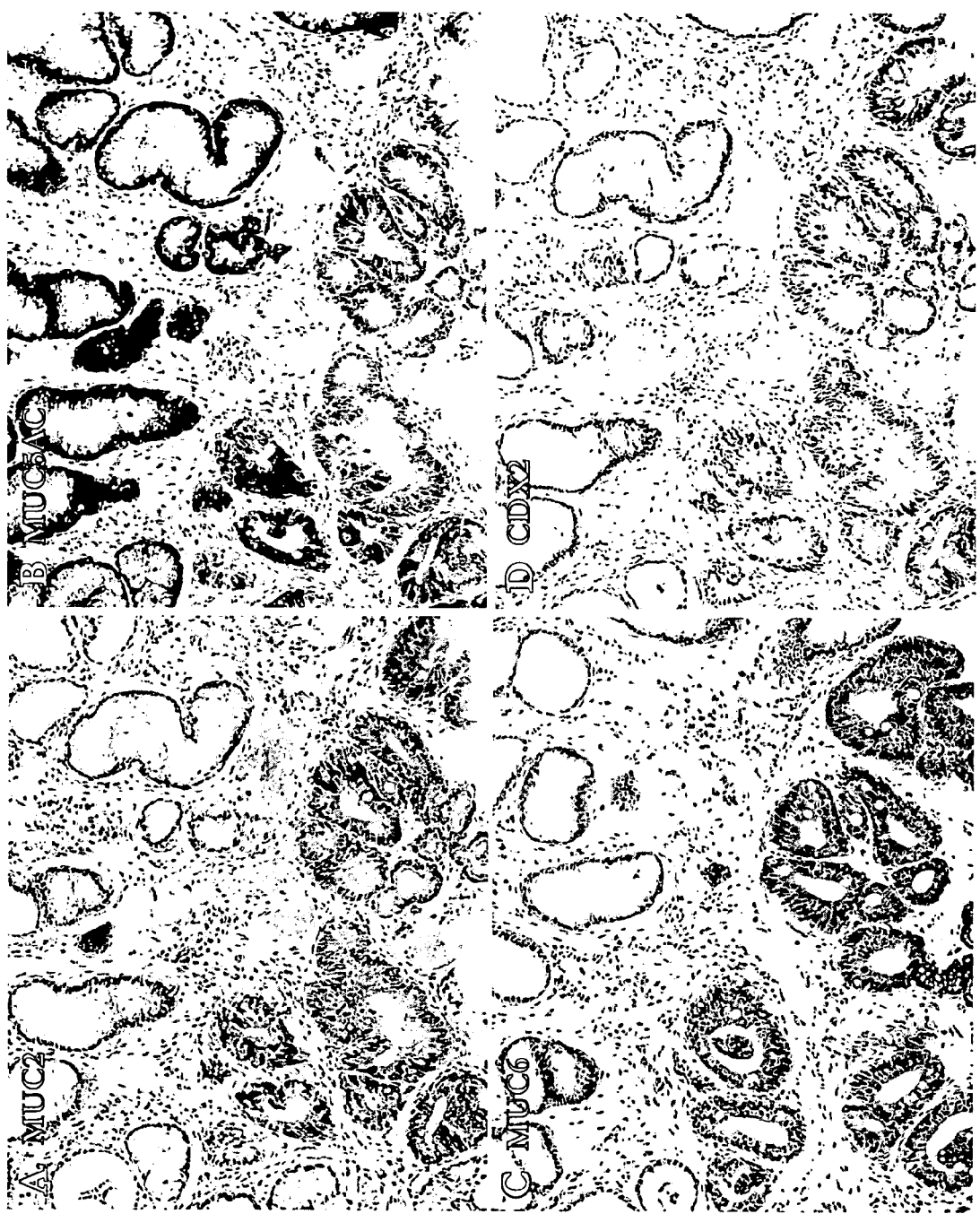
FIG. 7 depicts the immunohistochemistry staining of MUC2 (A), MUC5AC (B), MUC6 (C), and CDX2 (D) in gastric dysplasia.

FIG. 7 depicts gastric dysplasia. The lower third of each photo represents dysplasia having densely clustered nuclei. (A) shows the expression of MUC2, (B) shows the expression MUC5AC, (C) shows the expression of MUC6, and (D) shows the expression of CDX2. No CDX2 expression was detected. Some of the dysplastic cells express both gastric (MUC5AC, MUC6) and intestinal mucin (MUC2).

Figure 8:
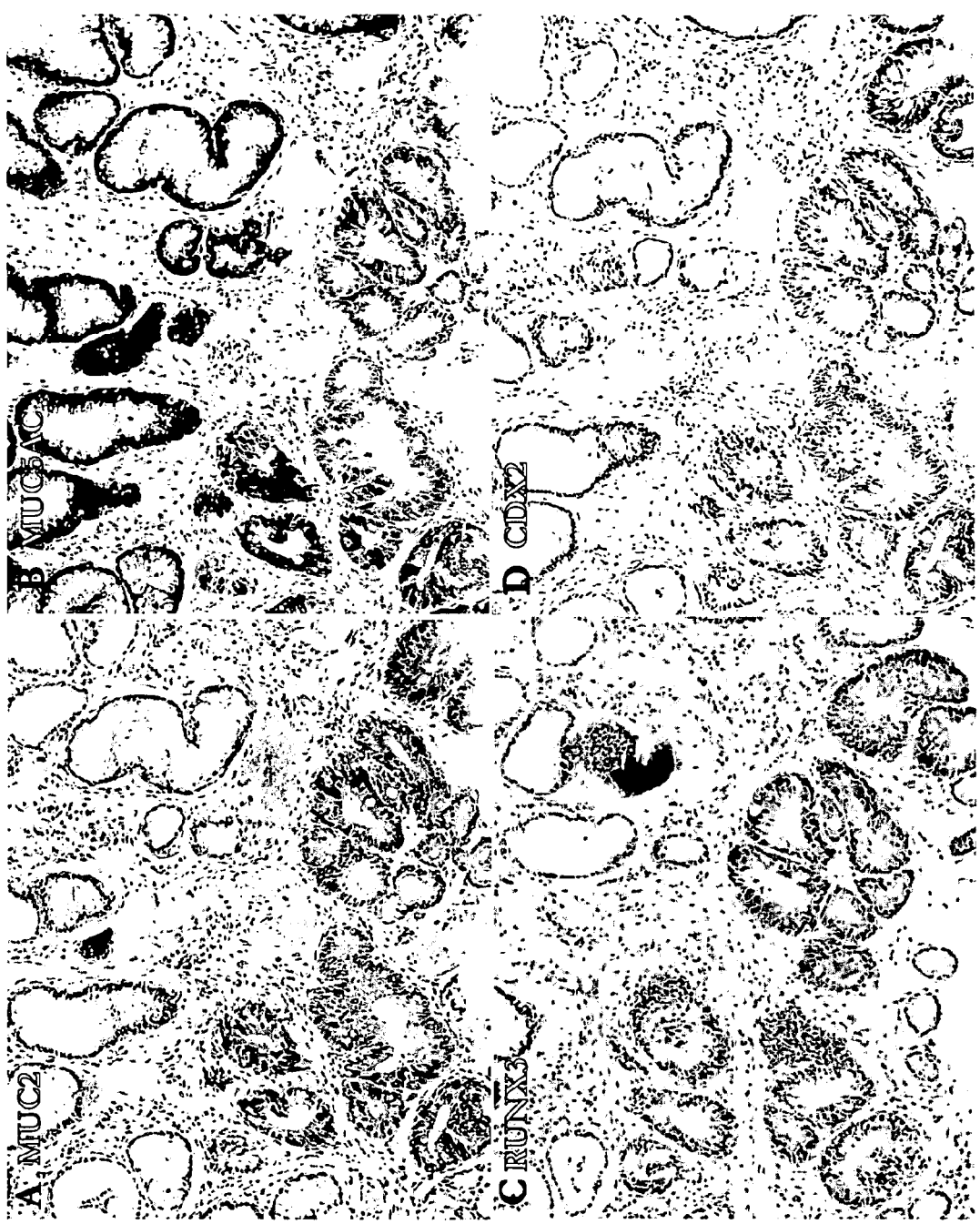
FIG. 8 depicts immunohistochemistry staining of MUC2 (A), MUC5AC (B), RUNX3 (C), and CDX2 (D) in gastric dysplasia.

FIG. 8 depicts the expression of RUNX3 in dysplasia. The figure corresponds to FIG. 7 with photo (C) of FIG. 7 (showing MUC6 expression) being replaced by a photo (C) showing RUNX3 expression. Expression of RUNX3 is lower than that in most of the intestinal metaplasia and a large fraction of RUNX3 is in the cytoplasm in dystplasia.

EXAMPLES

Example 1

Block of Differentiation of Mucous Neck Cells into Chief Cells in RUNX3-/- Fundic Glands Histological analyses were performed according to established standard procedures well known in the art.

Tissues were fixed with 4% paraformaldehyde in PBS, embedded in paraffin, and cut into 5 µm sections. For staining, the re-hydrated sections were placed in 1% Alcian Blue in 3% acetic acid (pH 2.5) for 30 min at 23° C. For immunohistochemical detections the following antibodies were used on re-hydrated sections: anti-MUC5AC (K-20; Santa Cruz, USA), anti-pepsinogen (Fukamachi, H. et al. (2001) *Biochem. Biophys. Res. Commun.* 280, 1069-1076), anti-MUC6 (HIK1083; Kanto Kagaku, Japan), anti-$H^+/K^+$ ATPase (1H9; MBL, USA), anti-ITF (Mashimo, H. et al. (1996) *Science* 274, 262-265), anti-MUC2 (Karlsson, N. G. et al. (1996) *Glycoconjugate J.* 13, 823-831), anti-villin (MAB1671; Chemicon, USA), anti-CDX2 (BioGenex, USA), and anti-PCNA (MAB424R; Chemicon, USA). Signals were detected by consecutive incubation with biotin-conjugated secondary antibodies and streptavidin-FITC (Roche Molecular Biochemicals, USA).

Staining for apoptotic cells was performed by using the Klenow-FragEL DNA fragmentation detection kit (Oncogene Research, USA) according to the recommendations of the manufacturer. Proliferating cells were labeled with 5-bromo-2-deoxyuridine (BrdU) using the BrdU Labeling and Detection Kit II (Roche Molecular Biochemicals, USA). BrdU (30 mg/kg body weight) was injected i.v. into mice. Four hours later the excised stomachs were fixed with 4% paraformaldehyde in PBS, embedded in paraffin, and cut into 5 µm sections.

The generation of RUNX3-/- mice has been described previously (Li, Q. L. et al. (2002), supra). RUNX3-/- mice of the C57BL/6 background die soon after birth due to starvation. RUNX3-/- mice of the BALB/c background, on the other hand, survive for at least 10 months. Therefore, the gastric phenotype of mutant mice of the BALB/c background was characterized by monitoring changes in the gastric mucosa. In the fundic area of wild type mice, a stem cell zone exists at the neck of glands. Thus, gastric mucosa could be separated into an upper (referred to as "Up", cf. also FIG. 1 (a)) and a lower compartment (referred to as "Lo"; cf. also FIG. 1 (a)) by the zone. Cells migrating towards the lumen undergo terminal differentiation to become surface epithelial cells, which are renewed every 3 to 4 days in both mice and humans (Karam, S. M. and Leblond, C. P. (1993) *Anat. Rec.* 236, 280-296). Cells migrating towards the gland base become mucous neck cells, which express MUC6 and low levels of pepsinogen.

These cells eventually differentiate into chief cells at the bottom of glands, which do not express MUC6 but do produce large amounts of pepsinogen (FIG. 1, (j, l)). The life span of chief cells is around 6 months. In the stomach of wild type adult mice, RUNX3 was maximally expressed in chief cells and, to a lesser degree, in surface epithelial cells, but at reduced levels in parietal cells and mucous neck cells (Li, O. L. et al. (2002), supra).

In the gastric mucosa of 6 months-old wild type mice, pepsinogen was fully expressed in chief cells, whereas it was detected at significantly reduced levels in the corresponding area in RUNX3-/- mice (compare FIG. 1 (g, i) with (f, h)). Instead, RUNX3-/- cells in virtually throughout the Lo, including the bottom area of the gland, were found to express MUC6 (FIG. 1 (m)). These results suggest that the differentiation of mucous neck cells into chief cells was blocked in the RUNX3-/- fundic glands. A determination of the cell number in each gland confirmed the decrease in chief cells and increase in mucous neck cells in mutant mice (FIG. 1 (p)). The cytoplasm of MUC6-expressing cells in the Lo of RUNX3-/- mucosa was filled with large amounts of mucin, and the cells were enlarged (FIG. 1 (m)).

Parietal cells secreting hydrochloric acid are also present in the Lo. In RUNX3-/- mice, they appeared smaller and morphologically somewhat distorted compared with those in wild type mice (compare FIG. 1 (o) with (n)). Since mucous neck cells are often enlarged in mutant mice due to a large amount of mucin in the cytoplasm, parietal cells appeared to be pressed between the mucous neck cells (compare FIG. 1 (o) with (n)). However, the number and the expression of proton pumps characteristic of parietal cells did not seem to be affected by the absence of the RUNX3 (FIG. 1 (p)). A reduction in the acidity of stomach epithelium can induce INTESTINAL METAPLASIA (Stemmermann, N. G. (1994), supra). Therefore, it was important to determine the acidity of the gastric mucosa of the mutant mice to confirm whether the parietal cells were functionally intact. Stomachs of the mutant mice varied in acidity from pH 2 to 5, although about half of them were lower than pH 3.0, while wild type stomachs were less variable, fluctuating between pH 2.0 and pH 3.0. Nevertheless, it was demonstrated that an intestinal phenotype (see below) was induced in RUNX3-/- gastric mucosa having an acidity below pH 3.0, ruling out the possibility that the induction of intestinal phenotype is due to a reduction in acidity rather than to the inactivation of RUNX3.

Example 2

Analysis of the Proliferation Capacity of Abnormally Expanded Mucous Neck Cells

Since mucous neck cells can proliferate, it was examined whether the abnormally expanded mucous neck cells throughout the Lo of mutant mice have growth potential. BrdU was found to be actively incorporated in a high proportion of MUC6-expressing cells, even in cells deep within the Lo of RUNX3-/- mouse stomach (compare FIG. 2 (b) with (a)). Immunodetection of proliferating cell nuclear antigen (PCNA) also showed the high capacity for proliferation of RUNX3-/- gastric epithelial cells in the Lo (compare FIG. 2 (d) with (c)). In contrast, the majority of cells in the Up did not incorporate BrdU or display PCNA reactivity, suggesting that Up cells were not experiencing accelerated growth.

Muc5AC is expressed in the foveolar epithelium of the stomach. The Up cells of RUNX3-/- mice showed a greatly reduced expression of Muc5AC compared with wild type cells (compare FIG. 1 (c, e) with (b, d)). The terminal differentiation of surface epithelial cells also appeared to be blocked in the absence of the RUNX3.

It is notable that the Up as well as the Lo mucosa of mutant mice exhibited hyperplasia (compare, for example, FIG. 2 (b, d) with (a, c)). Since in RUNX3-/- gastric epithelial cells of mice of the C57BL/6 background a lack of apoptosis was observed (Li, Q. L. et al. (2002), supra), it was examined whether apoptosis is reduced in BALB/c gastric epithelial cells that lack Runx3 activity. Indeed, a significant reduction in the frequency of apoptotic cells in the Up of mutant mice was observed, as compared with that in wild type mice (compare FIG. 2 (f) with (e)). Since this finding could provide a possible basis for the hyperplasia observed in the Up of mutant mice, it will be necessary to determine whether the cells in the Up can develop into cancer cells. Immunohistochemical observations demonstrated that the differentiation of endocrine cells in RUNX3-/- gastric epithelium, including gastrin-positive cells (G cells) of the pyloric area, was not affected (data not shown).

Example 3

Expression of Intestinal Marker Genes in Gastric Epithelial Cells

In RUNX3-/- mice, CDX2 was expressed throughout the gastric mucosa, both in the Up and Lo except for parietal cells (compare FIG. 3 (b) with (a)), although the level of expression varied considerably from cell to cell (FIGS. 3 (b), 4 (c)). In addition to CDX2, several other intestine-specific markers were examined. Intestinal trefoil factor (ITF), secreted throughout the small and large intestines, is considered to have an important role in the maintenance and repair of the intestinal mucosa (Mashimo, H. et al. (1996), supra) and is a marker of poor prognosis in gastric carcinoma (Yamachika, T. et al. (2002) *Clin. Cancer Res.* 8, 1092-1099). MUC2 is specifically expressed in the goblet cells of the small and large intestines (Karlsson, N. G. et al. (1996), supra). Alcian blue reacts with acidic mucins (i.e. sulphomucin and sialomucin; Reis, C. A. et al. (1999), supra) and is often used to detect intestinal markers. Villin is a structural protein of intestinal absorptive cells (Dudouet, B. et al. (1987) *J. Cell Biol.* 105, 359-369).

A significant expression of these intestinal markers was observed in the gastric mucosa of one month-old RUNX3-/- mice. However, Alcian Blue stained the gastric mucosa of mutant mice that were 3 months old and older (FIG. 3 (d, f)), whereas it did not stain the gastric mucosa of wild type mice 3 months (FIG. 3 (c)) or 6 months (FIG. 3 (e)) after birth. The earliest stage when Alcian Blue-positive cells were observed in RUNX3-/- gastric mucosa was around 10 weeks, and the maximal levels of RUNX3 expression in the gastric epithelial cells of wild type mice was observed after 8-10 weeks (data not shown). Up and Lo cells in 6 months-old mice were stained by Alcian Blue (FIG. 3 (f-h)). MUC2 was also detected in both Up and Lo cells of the mutant but not wild type mice (compare FIG. 3 (l) with (k)). The intestinal phenotype was first noted when the glandular structure was fully formed in the mouse stomach. The fact that RUNX3 is expressed most strongly in mature chief cells and surface epithelial cells suggests that it begins to exert its critical function around the time the gland structure is fully formed. Therefore, the RUNX3-/- phenotype may become evident around the time of gland maturation. Like CDX2, ITF was detected throughout 6 months-old RUNX3-/- gastric mucosa in both the Up and Lo and within the same gland (compare FIG. 3 (j) with (i)). Villin is expressed strongly in the Up and weakly in the Lo of Runx3-/- gastric epithelium (compare FIG. 3 (n, o) with (m)). The expression of CD10 (Groisman, G. M. et al. (2002) *Am. J. Surg. Pathol.* 26, 902-907) and alkaline phosphatase in RUNX3-/- gastric mucosa was undetectable (data not shown). Since the latter two markers are specific to small intestinal absorptive cells, the majority of the cells in the RUNX3-/- gastric mucosa that express these intestinal phenotypes are considered to be similar to colon epithelial cells. The structure of the pyloric glands, where human gastric cancer most frequently develops, is simpler than that of the fundic glands, in that only surface epithelial cells, proliferative cells, and mucoid cells expressing pepsinogen are present. Intestinalization of the mucosa was also observed in the RUNX3-/- pyloric region, as revealed by the expression of ITF (compare FIG. 3 (q, s) with (p, r)).

It is noteworthy that each gland of the mucosa is composed of cells derived from a single progenitor (Tatematsu, M. et al. (2003) *Cancer Sci.* 94, 135-141). The monoclonal origin of each gland thus makes it easier to interpret the complex phenotypes observed in knockout mice. In the RUNX3-/- gastric mucosa, almost all glands displayed a gastric (G) phenotype alone, an intestinal (I) phenotype alone or the mixture of these two (GI), which were manifested as Alcian Blue- and MUC6-positive cells (FIG. 4 (a-c)), and these cells were proliferative (FIG. 4 (d)). The appearance of the G, mixed GI, and I phenotypes appears to be stochastic in RUNX3-/- epithelial cells rather than chronological (Tatematsu, M. et al. (2003), supra). Since cells in a single gland presumably have identical genotypes, variation in the penetrance of the G and I phenotypes may be governed by epigenetic mechanisms (see below).

Dysplastic lesions were often found in RUNX3-/- mice at 10 months of age: the gastric epithelial cells were irregularly arranged, and contained hyperchromatic nuclei that were disproportionately large. Some cells penetrated through the muscularis mucosae towards the submucosa (FIG. 4 (e)). These cells expressed MUC6, a G marker, and were positive for Alcian Blue, an I marker (FIG. 4 (e, f)). They were highly proliferative (FIG. 4 (g)). These results indicate that cells exhibiting the mixed GI phenotype in the RUNX3-/- gastric epithelium at around 6 months of age are pre-cancerous in nature, and these cells undergo dysplastic changes presumably by acquiring further genetic or epigenetic changes.

From the results described above, the observations can be summarized in the model shown in FIG. 5. Mucous neck cells are blocked from differentiating into chief cells. At the same time, the lineage of differentiation is deregulated and these cells are induced to express I markers, although they continue to express a G marker. That is, the mucous neck cells that accumulate in the glands in the absence of Runx3 are no longer genuine gastric or intestinal cells. The appearance of both the G and I phenotypes in a single cell or in cells of a single gastric gland is often observed for INTESTINAL METAPLASIA of the human stomach. Together with their high capacity for proliferation, the developmentally blocked abnormal mucous neck cells expressing both G and I markers observed in the RUNX3-/- stomach are typically pre-cancerous. Indeed, the dysplasia observed in 6 to 10 month-old mutant mice exhibited the mixed GI phenotype. Cells destined to become surface epithelial cells are also unable to terminally differentiate and are resistant to apoptosis. Thus, it is feasible that developmentally blocked surface epithelial cells become cancer cells. Previously, it was demonstrated that RUNX3 is a major growth regulator of gastric epithelial cells (Li, Q. L. et al. (2002), supra). Here, evidence is provided that the gene is also a regulator of gastric epithelial cell differentiation.

A morphological hallmark of human INTESTINAL METAPLASIA is the presence of readily recognizable goblet cells. In the "intestinalization" in the RUNX3-/- gastric mucosa shown here, very few typical goblet cells were observed, despite the fact that widespread expression of intestinal markers including MUC2 was detected in these cells. There is a distinct difference between the inactivation of RUNX3 in the germ line of RUNX3-/- gastric mucosa and RUNX3 inactivation in human INTESTINAL METAPLASIA where it is a somatic event. In order for cells to acquire goblet cell morphology, RUNX3 might be required at certain stages in development. Goblet cell formation fails to occur in the absence of the MUC2 gene (Velcich, A. et al. (2002) *Science* 295, 1726-1729), the gene, which encodes the zinc-finger transcription factor Klf4 (Katz, J. P. et al. (2002) *Development* 129, 2619-2628), or the Math1 gene encoding a basic helix-loop-helix (bHLH) transcription factor (Yang, Q. et al. (2001) *Science* 294, 2155-2158). Math1 is also required for endocrine cell formation in the intestine but such cells were not affected in the stomach of RUNX3-/- mice (data not shown). Since MUC2 and Klf4 seem to be downstream targets of CDX2 (Dang, D. T. et al. (2001) *Oncogene* 20, 4884-4890; Mesquita, P. et al. (2003) *J. Biol. Chem.* 278, 51549-51556) and as both CDX2 and MUC2 are expressed in the stomach of RUNX3-/- mice, failure to form goblet cells does not seem to be due to a lack of Klf4 expression. RUNX3 may thus be required for other pathways in goblet cell formation.

In any event, it will be important to determine whether the appearance of goblet cells in gastric mucosa per se is causally related to gastric carcinogenesis or whether a more general induction of intestine-specific gene expression is required to induce pre-cancerous conditions. Nevertheless, the dramatic induction of intestine-specific genes in both cases warrants a direct comparison of the phenotypes of RUNX3-/- gastric mucosa and INTESTINAL METAPLASIA. The inactivation of RUNX3 is thus suggested to induce INTESTINAL METAPLASIA. Considering the fact that RUNX3 is a candidate for a gastric cancer tumor suppressor gene, INTESTINAL METAPLASIA must be a pre-cancerous state, wherein the inactivation of RUNX3 appears to trigger the carcinogenesis process.

The mechanism of gastric carcinogenesis triggered by the inactivation of RUNX3 suggested above is strikingly similar to that observed for RUNX1 inactivation. RUNX1 is required for the granulocytic differentiation of myeloid progenitor cells, and its inactivation is leukemogenic (Sakakura, C. et al. (1994) *Proc. Natl. Acad. Sci. USA* 91, 11723-11727). This observation is in line with the more general notion that the normal physiological functions of most oncogenes and tumor suppressor genes are to regulate differentiation and that cancer is a consequence of deregulated development and differentiation (Bishop, J. M. (1983) *Cell* 32, 1018-1020).

However, the link between INTESTINAL METAPLASIA and cancer may be based on complex interactions. In may cases of INTESTINAL METAPLASIA expression of RUNX3 was observed. Toward clarifying the relationship between RUNX3 expression and INTESTINAL METAPLASIA in human gastric epithelium, the expression of gastric mucins (MUC5AC, MUC6) and intestinal mucin (MUC2) we examined in relation to CDX2 expression in INTESTINAL METAPLASIA in human specimens (cf. FIG. 6). Interestingly, two distinct levels of CDX2 expression were found. Low levels of CDX2 were found to correlate with previously classified incomplete INTESTINAL METAPLASIA, in which both gastric and intestinal mucins are expressed (cf.

FIG. 7 and FIG. 8). This incomplete INTESTINAL METAPLASIA is considered to be particularly strongly associated with gastric cancer.

The observation that CDX2 is up-regulated in the gastric epithelial cells of RUNX3-/- mice suggests that RUNX3 negatively regulates CDX2, either directly or indirectly, in wild type gastric epithelial cells. In this regard Kim et al (2006, supra) have confirmed that there is no CDX2 expression in normal mucosa, but is detectable in both INTESTINAL METAPLASIA and carcinoma. It is noted that RUNX3 is expressed in wild-type intestinal epithelial cells but at levels lower than in gastric epithelial cells (data not shown). Therefore, the level of RUNX3 expression in intestinal cells may be too low to suppress CDX2. Alternatively, the sets of transcription factors expressed in intestinal and gastric epithelial cells that induce tissue-specific phenotypes may differ, such that the expression of CDX2 is independent of the expression of Runx3 in intestinal epithelial cells.

While it is not known whether the aberrant expression of CDX2 in stomach cells induces a pre-cancerous state, it is known that inactivation of the CDX2 gene induces intestinal tumor and colonic hamartoma (Beck, F. et al. (1999) Proc. Natl. Acad. Sci. USA 96, 7318-7323; Tamai, Y. et al. (1999) Cancer Res. 59, 2965-2970). CDX2 seems to function as a tumor suppressor in the intestine and colon, in contrast to its possible function in the stomach. In this regard, it is notable that cells in INTESTINAL METAPLASIA, which are likely to be pre-cancerous, express CDX2, whereas gastric cancer cells often do not. It appears that the expression of CDX2 tends to be turned off in cancer cells. It is also worth noting that CDX2 directs endodermal differentiation towards a caudal phenotype and that haploinsufficiency in the developing distal intestine leads to homeotic transformation to a more rostral endoderm phenotype (Beck, F. et al. (1999), supra). We have shown that inactivation of RUNX3 induces transdifferentiation in the opposite direction, from a gastric to an intestinal character. Further elucidation of the exact relationship between RUNX3 and CDX2 would shed light on the development of gastrointestinal tract tumors and gastric carcinogenesis.

A possible role for RUNX3 in lineage-specific gene expression has been found for T cell development (Taniuchi, I. et al. (2002) Cell 111, 621-633; Woolf, E. et al. (2003) Proc. Natl. Acad. Sci. USA 100, 7731-7736). Immature thymocytes lacking CD4 and CD8 co-receptors differentiate into doubly positive ($CD4^+CD8^+$) cells, which are selected to become either $CD4^+CD8^-$ helper cells or $CD4-CD8^+$ cytotoxic cells. A transcriptional silencer regulates the expression of CD4 in both immature and $CD4-CD8^+$ thymocytes. It has been shown that RUNX1 is required for active repression in doubly negative thymocytes, whereas RUNX3 is required for establishing epigenetic silencing in cytotoxic lineage thymocytes. Since RUNX3 is specifically required for lineage-specific CD4 silencing, it may be a key molecule involved in regulating lineage specificity. In the absence of RUNX3, $CD4-CD8^+$ cells do not arise, but $CD4^+CD8^+$ cells having a cytotoxic cell marker accumulate. In other words, these cells express a mixture of markers derived from two lineages, strikingly similar to what is observed for gastric epithelial cells in RUNX3-/- mice. If RUNX3 is required for the formation of a chromatin structure conducive to the expression of chief cell-specific or surface epithelial cell-specific genes, this may explain the failure of these cells to differentiate in RUNX3-/- mice. It may thus be interesting to investigate the possible roles of RUNX family genes in the assembly and remodeling of chromatin with respect to lineage-specific cell differentiation in order to understand the mechanisms by which these genes induce carcinogenic processes.

Example 4

Analysis of the Expression of Intestinal and Gastric Marker Genes in Tissue Samples from Patients with Intestinal Metaplasia and Gastric Dysplasia 70 surgically resected gastric adenocarcinoma samples and the corresponding non-cancerous tissues were obtained from the Department of Pathology and Surgery, National University of Singapore under a protocol approved by Institutional Review Board. There were 47 males and 23 females, aged 31-86 years (mean±SEM, 62.6±1.6). 38 intestinal metaplasia foci were found in the tissues of 26 cases, including 18 intestinal metaplasia foci just beside the tumor in 16 cases and 20 intestinal metaplasia foci on the non-cancerous tissues in 15 cases.

According to the Lauren-classification of gastric adenocarcinoma (Lauren, P., et al., (1965) supra), there were 45 intestinal type of gastric adenocarcinoma and 19 diffuse type of gastric adenocarcinoma. The other 6 cases were mucinous adenocarcinoma, displaying an intestinal-type pattern of infiltration. It was listed as an individual group because of its unique expression pattern of mucins. The 45 intestinal type of gastric adenocarcinoma were further classified into well differentiated (14 cases), moderately differentiated (11 cases) and poorly differentiated (20 cases).

In addition, 7 gastric dysplasia samples, 5 colon adenocarcinoma samples and the corresponding non-cancerous tissues were obtained from Department of Pathology and Surgery, National University of Singapore.

Histochemistry

The samples were fixed with 10% neutral-buffered formalin and embedded in paraffin. Paraffin-embedded samples were serially sectioned at 4 μm and mounted on slides. intestinal metaplasia was classified into complete type and incomplete type, using Alcian Blue (pH 2.5)/Periodic Acid-Schiff (AB/PAS) staining (Dako AB/PAS stain system, Dakocytomation, Carpinteria, Calif.). After deparaffinization and rehydration, the sections were incubated with Alcian Blue pH 2.5 for 30 minutes, followed by 0.5% Periodic Acid for 10 minutes and Schiff solution for 10 minutes. Then the sections were counterstained with modified Mayer's hematoxylin for 5 minutes, dehydrated with graded ethanols and mounted with coverslip. In complete intestinal metaplasia, only goblet cells were stained blue while the intermediate absorptive non-secretory cells were not stained. In incomplete intestinal metaplasia, the goblet cells were stained blue and the intermediate columnar cells were also stained with blue or pink.

Immunohistochemistry

After routine deparaffinization and rehydration of the slides, the antigen retrieval was done by the incubation in modified citrate buffer (target retrieval solution, Dakocytomation, Carpinteria, Calif.) at 96° C. for 40 minutes (for Muc2, Muc5AC, Muc6 and Ki67 antibodies) or at 121° C. for 20 minutes (for CDX2 antibody). During the optimization of the CDX2 staining protocol, it was observed that higher concentrations of CDX2 antibody, overnight incubation of primary antibody and antigen retrieval with EDTA buffer at 121° C. for 20 minutes could significantly enhance the CDX2 staining intensity in incomplete intestinal metaplasia and thus diminish the difference between incomplete intestinal metaplasia and complete intestinal metaplasia.

The sections were treated with 0.03% hydrogen peroxide for 5 minutes to block the endogenous peroxidase activity. The sections were then incubated with anti-CDX2 monoclonal antibody (1:100, Biogenex, San Ramon, Calif.), anti-Muc2 monoclonal antibody (1:100, Novocastra laboratories, Newcastle, UK), anti-Muc5AC monoclonal antibody (1:100, Novocastra laboratories, Newcastle, UK), anti-Muc6 monoclonal antibody (1:100, Novocastra laboratories, Newcastle, UK) or anti-Ki67 monoclonal antibody (1:100, Dakocytomation, Carpinteria, Calif.) at room temperature for 1 hour. The sections were incubated with peroxidase labeled polymer from Envision+System-HRP (DAB) kit (Dakocytomation, Carpinteria, Calif.) at room temperature for 1 hour. After development with diaminobenzedine, the sections were counterstained with hematoxylin, dehydrated with graded ethanols and mounted with coverslip.

Assessment of Staining in Cancer

At least 10 representative fields under high power magnification (×400) were chosen and more than 1000 cancer cells or, if the total number of cancer cells was below 1000, all available cancer cells were counted for each section.

The Ki67 proliferation index (Ki67 is an antigen detecting proliferating cells in the G1-, S- and G2-phase of the cell cycle) was defined as the percentage of Ki-67 positive cancer cells. Both qualitative and semi-quantitative approaches were used in scoring the staining of Muc2, Muc5AC, Muc6 and CDX2. Samples were classified as positive if >5% tumor cells stained positive and otherwise as negative.

Semi-quantitative scores were given as the score of percentage of positive cells plus the score of the staining intensity. The scoring criteria of the percentage of positive cells were as follows: 0, 0-5% positive cancer cells; 1, 6-25% positive cancer cells; 2, 26-50% positive cancer cells; 3, 51-75% positive cancer cells; 4, 76-100% positive cancer cells. The intensity score was given as follows: 0, no staining; 1, weak/equivocal staining; 2, mild staining; 3, moderate staining; 4, strong staining. The minimum score was 0 and the maximum score was 8.

Two experienced investigators independently examined the staining while blind to the clinicopathologica data. Different scores between the two investigators were observed in <15% of the cases and a consensus could be achieved in all the cases after discussion.

Statistical Analysis

The Fisher's exact test or the Chi-square test was used to calculate the difference of distribution in two or three groups. T-test or one-way ANOVA with bonferroni test was used to compare the means between 2 groups or among 3 groups. Difference at P<0.05 were considered to be statistically significant.

Results

The Expression of Muc2, Muc5AC, Muc6 and CDX2 in Normal Gastric Mucosa and Intestinal Metaplasia In normal gastric mucosa, Muc5Ac was expressed in the superficial foveolar epithelium and Muc6 was expressed in the mucous neck cells of the body and deeper glands of the antrum. Muc2 and CDX2 are not expressed in the normal gastric mucosa (Table 1, see below).

38 foci of intestinal metaplasia were classified into 19 foci of complete type and 19 foci of incomplete type by AB/PAS staining. Muc2 was expressed in the goblet cells in all intestinal metaplasia glands. Muc5AC was expressed in both goblet cells and columnar cells in incomplete intestinal metaplasia. It was also expressed in a few goblet cells but not absorptive cells in complete intestinal metaplasia. Muc6 was expressed in both goblet cells and columnar cells in several deeper glands of incomplete intestinal metaplasia (data not shown). This is in agreement with previous reports which showed complete intestinal metaplasia with de novo expression of intestinal mucin-Muc2 and decreased expression of gastric mucins while incomplete intestinal metaplasia with co-expression of intestinal and gastric mucins. In a few glands within the foci of complete intestinal metaplasia, Muc5AC and Muc6 were expressed in both goblet cells and columnar cells and this demonstrated the 'mosaic' pattern of intestinal metaplasia subtypes.

CDX2 expression was significantly lower in the foci of incomplete intestinal metaplasia than in the foci of complete intestinal metaplasia. Furthermore, within the mosaic foci of intestinal metaplasia, the CDX2 expression in the glands which expressed Muc5AC or Muc6 was significantly lower than the glands which did not express Muc5AC and Muc6 (data not shown). This indicates the decrease of CDX2 expression is consistent in every gland of incomplete intestinal metaplasia (cf. also FIG. 6).

The Expression of CDX2 in Normal Colon and Colon Cancer

The CDX2 protein was strongly expressed in normal colon epithelium, from superficial to deeper glands. 2 out of 5 colon cancer cases tested showed loss or significantly decreased CDX2 expression in cancer tissue compared with normal colon epithelium (data not shown). This further shows the tumor-suppressive role of CDX2 in colon. Considering the fact that incomplete intestinal metaplasia is associated with greater risk of gastric cancer compared with complete intestinal metaplasia, the decrease of CDX2 in incomplete intestinal metaplasia may be important in gastric carcinogenesis. The further decrease or loss of CDX2 in the majority of gastric dysplasia and gastric cancer further illustrates the tumor-suppressive role of CDX2 in stomach as well as in colon.

The Expression of Muc2, Muc5AC, Muc6 and CDX2 in Gastric Cancer

The results were summarized in Table 2. The Muc2 protein was expressed in 100% mucinous type of gastric cancer (6/6, score 7.17±0.54) and significantly higher than that in intestinal type (51%, 23/45, score 3.24±0.49) (P<0.05).

The CDX2 score of the gastric cancers with positive Muc2 expression was significantly higher than that of the gastric cancers with negative Muc2 expression (P<0.001). However, the CDX2 score of the gastric cancers with positive Muc5AC or Muc6 expression was significantly lower than that of the gastric cancers with negative Muc5AC or Muc6 expression respectively.

Using Muc5AC and Muc6 as the markers of gastric differentiation and Muc2 as the marker of intestinal differentiation. The gastric cancer were classified into four categories: G, positive for one or both gastric mucins (Muc5AC and Muc6) only; GI, positive for intestinal mucin (Muc2) and at least one of the gastric mucins (Muc5AC and Muc6); I, positive for intestinal mucin (Muc2) only; N, none of the Muc2, Muc5AC and Muc6 is positive. The 70 gastric cancer cases were classified into 20 cases of G type, 26 cases of GI type, 14 cases of I type and 10 cases of N type. The CDX2 score in I type of gastric cancer was the highest among the four groups, which is significantly higher than that in GI type of gastric cancer. The latter was also significantly higher than that in G type of gastric cancer.

The Expression of Muc2, Muc5AC, Muc6 and CDX2 in Gastric Dysplasia

Out of the 7 biopsies of gastric dysplasia, only 1 case of non-intestinal metaplasia dysplasia showed marked CDX2 expression. In the other 6 dysplastic intestinal metaplasia cases, 3 cases showed lost and the other 3 cases showed significantly decreased CDX2 protein expression. The non-intestinal metaplasiadysplasia was just next to the incomplete IM glands and 5 out of the 6 dysplastic intestinal metaplasia cases showed Muc 5AC and/or Muc6 expression in the dysplastic glands, suggesting the close relationship between dysplasia and incomplete intestinal metaplasia (FIG. 7).

The Ki67 Expression in Normal Gastric Mucosa, Intestinal Metaplasia and Gastric Cancer Ki67 positive cells were found in the neck region of normal gastric mucosa. Ki67 was also expressed in some cells in deeper glands of intestinal metaplasia, with no significant difference between complete intestinal metaplasia and incomplete intestinal metaplasia. The Ki67 index of cancer was not significantly related with the clinicopathological data and the expression of Muc2, Muc5AC, Muc6 and CDX2.

Correlation of the Expression of CDX2 and Mucins with Clinicopathological Features The age of the patients with intestinal type of gastric cancer (66.2±1.6) was significantly higher than that of the patients with diffuse type of gastric cancer (54.6±3.7) (P<0.01). There was no significant association between the expression of Muc2, Muc5AC, Muc6 and CDX2 and the clinipathological data, including age and sex.

The listing or discussion of a previously published document in this specification should not necessarily be taken as an acknowledgement that the document is part of the state of the art or is common general knowledge. All documents listed are hereby incorporated herein by reference in their entirety.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

TABLE 1

The expression pattern of Muc2, Muc5Ac, Muc6 and CDX2 in normal gastric mucosa, complete IM, incomplete IM and normal colonic mucosa

| | Muc2 | Muc5AC | Muc6 | CDX2 |
|---|---|---|---|---|
| Normal gastric mucosa | — | +in superficial foveolar epithelium | +in the mucous neck cells of the body and deeper glands of the antrum | — |
| Complete IM | +in goblet cell | −or + in few goblet cells | — | Strongly positive in both goblet cells and columnar cells |
| Incomplete IM | +in goblet cell | +in both goblet cells and columnar cells | +in both goblet cells and columnar cells | Weakly positive in both goblet cells and columnar cells |
| Normal colonic mucosa | +in goblet cell | — | — | Strongly positive in every cell |

TABLE 2

The expression of Muc2, Muc5AC, Muc6 and CDX2 in gastric cancer

| | | | Muc2 | | Muc5AC | | Muc6 | | CDX2 | |
|---|---|---|---|---|---|---|---|---|---|---|
| | Gastric cancer type | | Positive cases (%) | Score* | Positive cases (%) | Score* | Positive cases (%) | Score* | Positive cases (%) | Score* |
| Intestinal type | Total (45)# | | 23 (51%) | 3.24 ± 0.49 | 23 (51%) | 3.47 ± 0.53 | 18 (40%) | 2.22 ± 0.42 | 30 (67%) | 3.20 ± 0.39 |
| | Differentiation | Well (14) | 10 (71%) | 4.57 ± 0.85 | 7 (50%) | 3.36 ± 0.96 | 5 (36%) | 2.07 ± 0.79 | 11 (79%) | 4.00 ± 0.69 |
| | | Moderate (11) | 4 (36%) | 2.09 ± 0.88 | 7 (64%) | 4.27 ± 1.05 | 5 (45%) | 2.36 ± 0.82 | 6 (55%) | 2.27 ± 0.73 |
| | | Poor (20) | 9 (45%) | 2.95 ± 0.77 | 9 (45%) | 3.10 ± 0.81 | 8 (40%) | 2.25 ± 0.64 | 13 (65%) | 3.15 ± 0.61 |
| Diffuse type (19) | | | 11 (58%) | 3.95 ± 0.82 | 14 (74%) | 5.42 ± 0.79 | 8 (42%) | 2.63 ± 0.75 | 8 (42%) | 2.37 ± 0.68 |

TABLE 2-continued

The expression of Muc2, Muc5AC, Muc6 and CDX2 in gastric cancer

| | Muc2 | | Muc5AC | | Muc6 | | CDX2 | |
|---|---|---|---|---|---|---|---|---|
| Gastric cancer type | Positive cases (%) | Score* | Positive cases (%) | Score* | Positive cases (%) | Score* | Positive cases (%) | Score* |
| Mucinous type (6) | 6 (100%)^ | 7.17 ± 0.54^ | 3 (50%) | 3.83 ± 1.72 | 0 (0%) | 0 ± 0 | 5 (83%) | 4.33 ± 0.99 |
| Total (70) | 40 (57%) | 3.77 ± 0.41 | 40 (57%) | 4.03 ± 0.43 | 26 (37%) | 2.14 ± 0.34 | 43 (61%) | 3.07 ± 0.33 |

The figure in the brackets is the number of cases.
*Scores were expressed as the mean ± the standard error of the mean
^$P < 0.05$ when compared with the other in the same column

What is claimed is:

1. A method for identifying a compound inhibiting the development of an intestinal phenotype in one or more gastric cells which are in a precancerous state, the method comprising:
   (a) contacting said one or more gastric cells with a solution supposed to contain at least one compound to be identified;
   (b) incubating said cells for a predetermined period of time; and
   (c) measuring the expression of the RUNX3 gene and the expression of said one or more intestinal marker genes,
   wherein said intestinal phenotype is characterized by the loss of expression of the RUNX3 gene and a change in the expression of one or more intestinal marker genes such that the level of said one or more marker genes is characteristic of said intestinal phenotype;
   wherein a compound inhibiting the development of an intestinal phenotype of one or more gastric cells is identified.

2. The method of claim 1, wherein step (c) further comprises detecting the expression of one or more gastric marker genes.

3. The method of claim 1, further comprising:
   (d) comparing the result of the measurement obtained in step (c) with that of a control measurement without the addition of said solution supposed to contain said at least one compound to be identified; and
   (e) identifying the compound inhibiting the development of said intestinal phenotype.

4. The method of claim 1, wherein the compound inhibits or abolishes the expression of at least one of the one or more intestinal marker genes.

5. The method of claim 1, wherein the one or more cells are epithelial cells.

6. The method of claim 1, wherein the intestinal phenotype is characterized by a retained capacity to proliferate.

7. The method of claim 6, wherein the intestinal phenotype is a precursor of gastric cancer.

8. The method of claim 1, wherein the loss of expression of the RUNX3 gene is detected by measuring the degree of methylation of the exon 1 region of the RUNX3 gene and/or determining the absence of a RUNX3 gene product, wherein the gene product is selected from the group consisting of an mRNA and a protein.

9. The method of claim 8, wherein the absence of the RUNX3 protein is determined by using an anti-RUNX3 antibody.

10. The method of claim 1, wherein the one or more intestinal marker genes are selected from the group of genes encoding MUC2 and CDX2.

11. The method of claim 2, wherein the one or more gastric marker genes are the genes encoding MUC6 or MUC5AC.

12. The method of claim 10, wherein the expression of the one or more intestinal marker genes is detected by determining the presence of the gene products encoding said marker genes, wherein the gene products are selected from the group consisting of an mRNA and a protein.

13. The method of claim 12, wherein the presence of a protein encoded by an intestinal marker gene is determined by using a specific antibody.

* * * * *

UNITED STATES PATENT AND TRADEMARK OFFICE
CERTIFICATE OF CORRECTION

| | | |
|---|---|---|
| PATENT NO. | : 7,611,847 B2 | Page 1 of 1 |
| APPLICATION NO. | : 11/445925 | |
| DATED | : November 3, 2009 | |
| INVENTOR(S) | : Yoshiaki Ito et al. | |

It is certified that error appears in the above-identified patent and that said Letters Patent is hereby corrected as shown below:

IN THE CLAIMS

Column 25, lines 17-36 please amend Claim 1 as follows:

--1. A method for identifying a compound inhibiting the development of an intestinal phenotype in one or more gastric cells which are in a precancerous state, the method comprising:

(a) contacting said one or more gastric cells with a solution supposed to contain at least one compound to be identified;

(b) incubating said cells for a predetermined period of time; and (c) measuring the expression of the RUNX3 gene and the expression of [[said]] one or more intestinal marker genes, wherein said intestinal phenotype is characterized by the loss of expression of the RUNX3 gene and a change in the expression of one or more intestinal marker genes such that the level of said one or more marker genes is characteristic of said intestinal phenotype; wherein a compound inhibiting the development of an intestinal phenotype of one or more gastric cells is identified.--

Signed and Sealed this

Thirteenth Day of April, 2010

David J. Kappos
*Director of the United States Patent and Trademark Office*